US009226663B2

(12) United States Patent
Fei

(10) Patent No.: US 9,226,663 B2
(45) Date of Patent: Jan. 5, 2016

(54) SYSTEMS AND METHODS FOR OPTICAL ISOLATION IN MEASURING PHYSIOLOGICAL PARAMETERS

(71) Applicant: Physical Enterprises, Inc., Vancouver (CA)

(72) Inventor: Ming Shun Fei, Coquitlam (CA)

(73) Assignee: Physical Enterprises, Inc., Vancouver, British Columbia (CA)

( * ) Notice: Subject to any disclaimer, the term of this patent is extended or adjusted under 35 U.S.C. 154(b) by 0 days.

(21) Appl. No.: 14/531,573

(22) Filed: Nov. 3, 2014

(65) Prior Publication Data

US 2015/0282713 A1 Oct. 8, 2015

Related U.S. Application Data

(63) Continuation-in-part of application No. 14/468,916, filed on Aug. 26, 2014.

(60) Provisional application No. 61/976,388, filed on Apr. 7, 2014.

(51) Int. Cl.
*A61B 5/00* (2006.01)
*A61B 5/021* (2006.01)
*A61B 5/024* (2006.01)

(52) U.S. Cl.
CPC ............ *A61B 5/0059* (2013.01); *A61B 5/02141* (2013.01); *A61B 5/02438* (2013.01); *A61B 5/6824* (2013.01); *A61B 5/02427* (2013.01); *A61B 5/6802* (2013.01); *A61B 5/7203* (2013.01)

(58) Field of Classification Search
None
See application file for complete search history.

(56) References Cited

U.S. PATENT DOCUMENTS

| 3,769,974 | A | 11/1973 | Smart et al. | |
|---|---|---|---|---|
| 4,880,304 | A | 11/1989 | Jaeb et al. | |
| 5,130,531 | A | 7/1992 | Ito et al. | |
| 5,237,994 | A | 8/1993 | Goldberger | |
| 7,067,893 | B2 | 6/2006 | Mills et al. | |
| 2012/0197093 | A1* | 8/2012 | Leboeuf et al. | 600/301 |
| 2013/0060098 | A1* | 3/2013 | Thomsen et al. | 600/301 |
| 2014/0142403 | A1* | 5/2014 | Brumback et al. | 600/324 |
| 2014/0206976 | A1* | 7/2014 | Thompson et al. | 600/391 |
| 2014/0221854 | A1* | 8/2014 | Wai | 600/508 |
| 2014/0288435 | A1* | 9/2014 | Richards et al. | 600/479 |

FOREIGN PATENT DOCUMENTS

| WO | 2011051888 | 5/2011 |
|---|---|---|
| WO | 2013106607 | 7/2013 |

* cited by examiner

*Primary Examiner* — Unsu Jung
*Assistant Examiner* — Carolyn Pehlke
(74) *Attorney, Agent, or Firm* — Clayton, McKay & Bailey, PC

(57) ABSTRACT

Described herein are systems and methods for optically isolating components of an optical sensor in physiological monitoring devices worn by a user to sense, measure, and/or display physiological information. An optical sensor may be mounted in the rear face of the device, emit light proximate a targeted area of a user's body, and detect light reflected from the targeted area. Optically isolating structure may be located at least partially between one or more components of the optical sensor to ensure that light detected by the sensor is light reflected from the targeted area rather than light emitted directly from a light source and/or ambient light. The optically isolating structure may, in some cases, extend between a contact surface of the monitoring device to a base portion of the sensor components or a surface of a circuit board to which the sensor components are mounted.

15 Claims, 12 Drawing Sheets

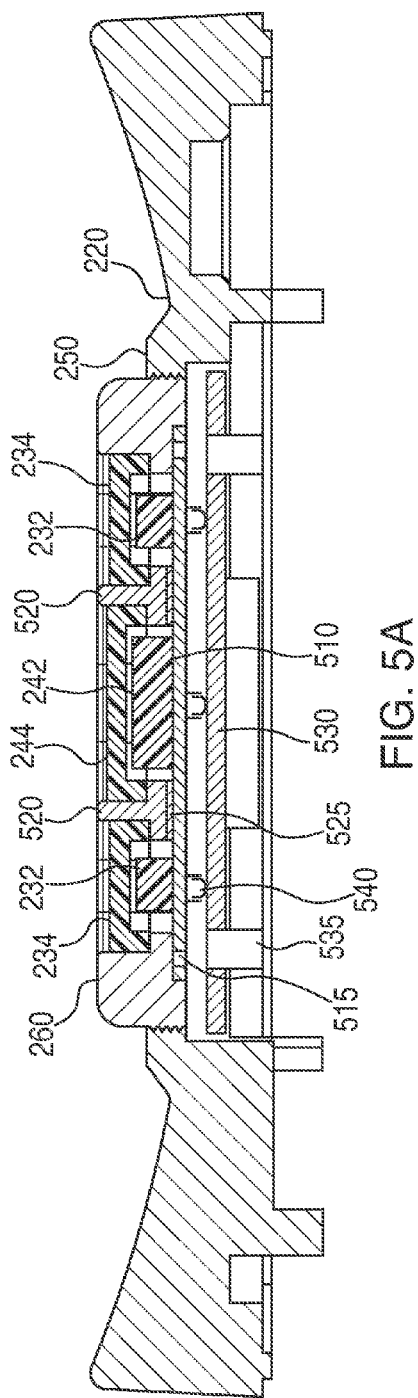
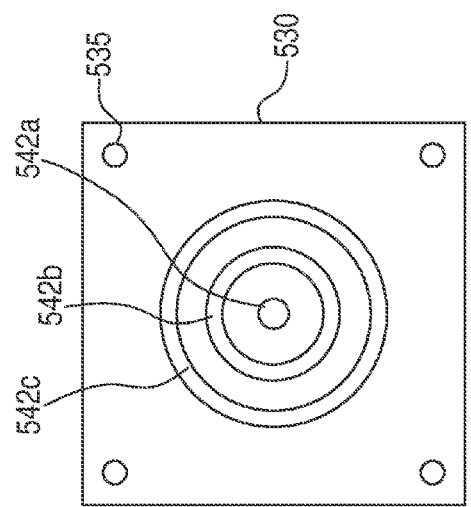
FIG. 5A
FIG. 5B

SYSTEMS AND METHODS FOR OPTICAL ISOLATION IN MEASURING PHYSIOLOGICAL PARAMETERS

This is a continuation-in-part application of U.S. patent application Ser. No. 14/468,916, filed Aug. 26, 2014, which claims the benefit of priority to U.S. Provisional Patent Application No. 61/976,388, filed Apr. 7, 2014, both of which are expressly incorporated herein by reference.

FIELD OF THE DISCLOSURE

The embodiments relate generally to systems and methods that use non-invasive electro-optical technology for sensing and measuring physiological parameters and, more specifically, systems and methods for optically isolating light reflected from a user's tissue from light emitted directly from a light source during the sensing and/or measuring physiological parameters.

BACKGROUND

Many portable devices have been developed in which optical sensors are used to detect variation in blood flow through arteries or blood volume in subcutaneous tissue. Applications include the monitoring of heart rate, glucose level, apnea, respiratory stress, and other physiological conditions. The optical sensors often comprise one or more light sources that illuminate a targeted portion of the human body and one or more associated optical detectors that receive a portion of the optical energy emitted by the light sources.

There are two basic types of such arrangements. In transmissive sensor arrangements, a relatively thin portion of the body such as the tip of the finger or the earlobe is positioned between a light source and a photo detector. Light that passes through the body tissue impinges on the photo detector resulting in an electrical signal that is synchronized to each heartbeat. In reflective sensor arrangements, a sensor that includes one or more light sources located in spaced apart juxtaposition with a photo detector is positioned against a targeted area of the body. Optical energy emitted by the light sources passes through the skin of the targeted tissue region, is scattered, partially absorbed, and is reflected by blood flowing through arteries and other vascular structure. The reflected optical energy is in effect modulated in accordance with blood flow in the targeted area and detected by the photo detector. The detected reflection can then be used to produce a signal pulse that is indicative of a physiological parameter such as a heartbeat. In both transmissive and reflective arrangements, the signal produced by the photo detectors is processed to display or otherwise provide a real-time indication of the monitored physiological parameter.

One area of growing interest in the use of physiological monitors is with respect to personal wellness and/or physical exercise for purposes of fitness training, weight loss, or monitoring general health. Technological advances relating to optical sensors, signal processing, and display devices have made it possible to realize small, light-weight physiological monitors that can be embodied as devices that may be comfortably worn by a user. Such wearable devices may include, for example, wrist watches, bracelets, and arm bands.

Providing physiological monitors for wellness and physical exercise applications is subject to numerous design and manufacturing considerations. For example, the electronic circuitry for processing the signal produced by the photo detector and displaying an indication of the monitored parameter must operate at a low power level to provide adequate battery life while simultaneously providing sufficient accuracy. Constraints relating to the physical design of such monitors are not limited to the challenges of packaging the electronics and display units in an arrangement that can be easily and comfortably worn by a user. Special considerations and constraints are present with respect to incorporation of the optical sensor. For example, the light sources and photodiode of the optical sensor must be optically isolated from one another. Otherwise, the photo detector will receive optical energy that is not modulated by a user's heartbeat, which can result in an unwarranted increase in electrical design requirements and/or seriously affect monitoring accuracy and power requirements. Similarly, optimal performance requires that the optical sensor be firmly positioned against the user's skin so that light emitted by a light source may pass through the skin and, additionally, so that ambient light does not reach an associated photo detector. Firmly positioning the optical sensor against the user's skin also is important with respect to preventing movement of the sensor that can affect the accuracy of the monitoring device and/or interrupt its operation. Additionally, the optical sensor should be securely retained by the monitoring device to maintain physical integrity and facilitate satisfactory waterproofing of the entire monitor.

Because of the above mentioned design and manufacturing considerations, as well as others that are known to designers and manufacturers, a need exists for improved techniques for incorporating optical sensor arrangements in physiological monitoring devices. Moreover, improved device and techniques are needed to ensure the accuracy, reliability, and durability of such devices.

SUMMARY OF THE DISCLOSURE

In accordance with certain embodiments of the present disclosure, optical sensor arrangements suited for use in physiological monitoring devices that are used for physical training, exercise, and/or general wellness monitoring are disclosed. In some embodiments, the monitoring devices may be a wrist watch, bracelet, or arm band comprising one or more optical sensor arrangements. Each optical sensor arrangement may comprise one or more light sources and/or photo detectors. In such embodiments, the light sources may comprise two or more spaced apart light emitting diodes (LEDs). Each photo detector may be, for example, a photodiode. In some embodiments, each photodiode may be positioned near a corresponding LED or between a corresponding pair of LEDs.

In one embodiment, the one or more light sources and/or photo detectors may be mounted in one or more transparent lenses that may be installed in a portion of a monitoring device configured for placement in contact with a user's skin. In other embodiments, one or more of lenses 234 and 244 may comprise an epoxy layer or encasement poured or placed into caseback 220 rather than a glass or plastic lens. Such an epoxy layer may be pre-formed or formed with a respective light source or optical detector positioned within caseback 220. For example, a liquid, semi-liquid, or gel-like epoxy may be poured over one or more of the light sources and/or photo detectors in caseback 220. The epoxy may then solidify into an epoxy layer that may completely or partially encase or encapsulate the one or more light sources and/or photo detectors. In other embodiments, the epoxy layer may be separated from the respective LED 232 or photodiode 242 by a barrier or by space.

In another aspect, the light source(s) and photo detector(s) may be positioned by and mounted to a printed circuit board. In one embodiment, the printed circuit board may be installed in the interior of the monitor and the lenses may be maintained in the monitor caseback. Portions of the caseback may extend outward to contact the printed circuit in a region between the one or more light sources and the one or more photo detectors to prevent light emitted by the light sources from being directly detected by the photo detectors. In some embodiments, these outwardly extending portions of the caseback may be barrier walls that optically isolate the one or more LEDs from the one or more photo detectors. Such a configuration may ensure that light detected by the one or more photo detectors is light that has been reflected by a user's tissue rather than light emitted directly from the one or more light sources (whether that light has traveled across the user's tissue or across the printed circuit). In embodiments in which the lenses comprise an epoxy layer poured over the one or more light sources and/or photo detectors, the barrier walls may also serve as forms for accepting the liquid, semi-liquid, or gel-like epoxy. Such forms may dictate the shape of the solidified lenses and/or prevent the liquid, semi-liquid, or gel-like epoxy from spilling into other portions of the caseback or monitoring device.

In further embodiments, a pliant opaque layer of tape or sponge-like material may be positioned on the printed circuit board such that the outwardly extending portions of the caseback and/or barrier walls may contact the opaque layer to further ensure optical isolation of the light sources and photo detectors. In particular, the opaque layer may further prevent light emitted from the one or more light sources from traveling along the surface of the printed circuit board and reaching the one or more photo detectors without first traveling into the user's tissue and being reflected back to the one or more photo detectors.

In other embodiments, the outwardly extending portions of the caseback and/or the barrier walls may comprise other structure or features to facilitate accurate and reliable monitoring of one or more physiological parameters. For instance, the barrier walls may comprise one or more abutment surfaces configured for supporting a lens within an aperture of the caseback. Alternatively, the abutment surfaces may be configured for maintaining the lenses within caseback in embodiments where the lenses are first poured into the apertures of the caseback in a liquid, semi-liquid, or gel-like state.

Additional objects and advantages of the present disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are illustrative and explanatory only and are not restrictive of the claims.

The accompanying drawings, which are incorporated in and constitute a part of this specification, illustrate several embodiments and together with the description, serve to explain the principles of the disclosure.

BRIEF DESCRIPTION OF THE DRAWINGS

FIG. 5A depicts some aspects of an illustrative embodiment of an apparatus as described herein.

FIG. 5B depicts some aspects of an illustrative embodiment of an apparatus as described herein.

DESCRIPTION OF THE EMBODIMENTS

Figure 1:
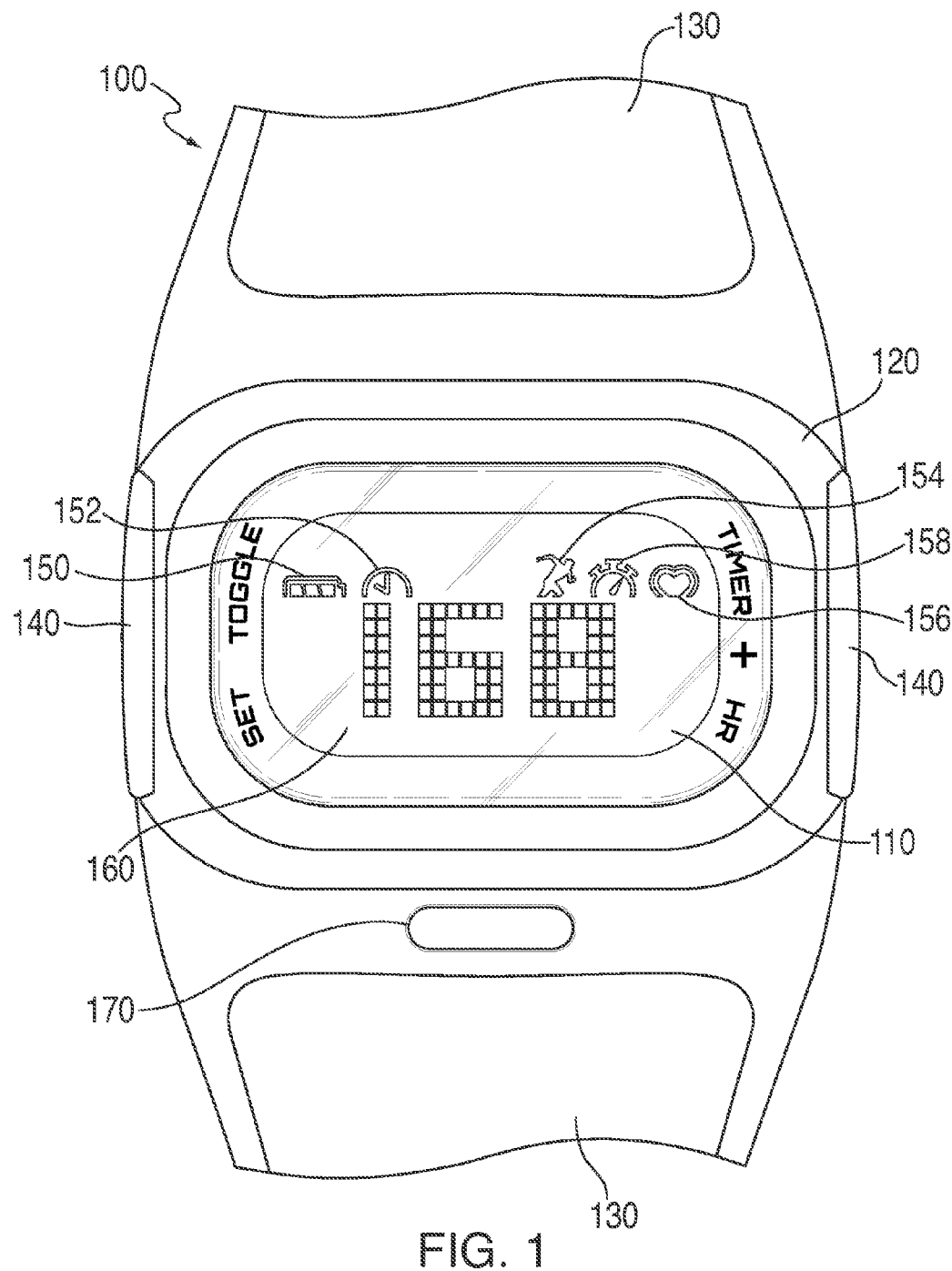
FIG. 1 depicts some aspects of an illustrative embodiment of an apparatus as described herein.

Disclosed herein are embodiments of an apparatus for sensing, measuring, and displaying physiological information. In one aspect, the apparatus may comprise an optical sensor incorporated into a wearable device. The optical sensor may be incorporated at a location of the wearable device such that, in use, a surface of the optical sensor may be adjacent or in close proximity to a targeted area of a user's body. In one embodiment, the optical sensor may comprise one or more light sources for emitting light proximate the targeted area and one or more optical detectors for detecting reflected light from the targeted area.

In another aspect, the optical sensor may be incorporated into the wearable device such that at least a portion of the optical sensor may protrude or extend beyond at least a portion of a device housing. In some embodiments, a height which the portion of the optical sensor may extend beyond the device housing may be fixed. In alternative embodiments, the height which the portion of the optical sensor may extend beyond the device housing may be adjustable. The adjustment of the protrusion height may be manually performed by the user, automated, or manually in some aspects and automated in other aspects.

In a further aspect, by allowing a user to customize the protrusion height associated with the optical sensor, a customized fit of the wearable device may be achieved. Moreover, a desirable level of contact and/or pressure between the inward facing surface of the optical sensor and the targeted area may be achieved. This, in turn, may result in more reliable and accurate sensing, measuring, and displaying of physiological information.

In one embodiment, the physiological information may be heart rate information. In other embodiments, the physiological information may be blood pressure information. Alternatively, the physiological information may be any information associated with a physiological parameter derived from information received by the wearable device. Regardless, the physiological information may be used in the context of, for example, athletic training, physical rehabilitation, patient monitoring, and/or general wellness monitoring. Of course, these examples are only illustrative of the possibilities and the device described herein may be used in any suitable context.

While the systems and devices described herein may be depicted as wrist worn devices, one skilled in the art will appreciate that the systems and methods described below can be implemented in other contexts, including the sensing, measuring, and display of physiological data gathered from a device worn at any suitable portion of a user's body, including but not limited to, other portions of the arm, other extremities, the head, and/or the chest.

Reference will now be made in detail to certain illustrative embodiments, examples of which are illustrated in the accompanying drawings. Wherever possible, the same reference numbers will be used throughout the drawings to refer to the same or like items.

FIG. 1 depicts an illustrative embodiment of an apparatus 100. In one aspect, apparatus 100 may be a physiological monitor worn by a user to sense, collect, monitor, and/or display information pertaining to one or more physiological parameters. In the depicted embodiment, apparatus 100 may comprise a wrist watch. In alternative embodiments, apparatus 100 may be a bracelet or an arm band. In further embodiments, apparatus 100 may be any wearable monitor device configured for positioning at a user's wrist, arm, another extremity of the user, or some other area of the user's body.

In another aspect, apparatus 100 may comprise an optical sensor assembly 210 (depicted in FIG. 2) and components for processing and displaying one or more physiological parameters of a user and/or other information that may or may not be related to exercise, physical training sessions, or general wellness. For example, in one embodiment, apparatus 100 may sense, process, and/or display heart rate information. In a further aspect, apparatus 100 may house a display unit 110 for displaying or otherwise conveying information to the user. In one embodiment, display unit 110 may comprise a dot matrix liquid crystal display. In alternative embodiments, display unit 110 may comprise some other suitable display.

In a further aspect, apparatus 100 may comprise a casing 120 and one or more bands 130 extending from opposite edges of casing 120 for securing apparatus 100 to the user. In one embodiment, band(s) 130 may comprise an elastomeric material. In alternative embodiments, band(s) 130 may comprise some other suitable material, including but not limited to, a fabric or metal material.

Apparatus 100 may further comprise one or more switches 140 operable for accepting input from the user. Switches 140 may comprise any suitable device for accepting input from the user including, but not limited to, a switch, button, touchscreen, or sensor. FIG. 1 depicts a pair of opposing switches 140, one positioned on either side of casing 120. Other embodiments, however, may comprise fewer or additional switches. Moreover, the switches may be located at any suitable location on apparatus 100.

In further embodiments, switches 140 may be incorporated into display unit 110. For example, switches 140 may comprise "soft" buttons configured to accept input from the user via a touchscreen.

In another aspect, the user may manipulate switches 140 for setting the time display, establishing the operational mode of the heart rate monitor, and/or otherwise configuring/interacting with apparatus 100 during use.

Casing 120 may further comprise switch indicators for providing the user information regarding each switch. In one embodiment, casing 120 may comprise words and/or symbols such as "set," "toggle," "timer," "+," and "HR" corresponding to the switches and providing the user with an indication of a function that may be achieved by manipulation of the respective switch. Of course, the switch indicators depicted in FIG. 1 are only illustrative of the possibilities. Casing 120 may comprise no, fewer, additional, or alternative indicators.

Display unit 110 may further comprise one or more small icons for conveying information to the user. In one embodiment, the one or more icons may be located in an upper portion of display 110 to indicate operational and/or conditional aspects of apparatus 100. For example, an icon 150 may be illuminated whenever the watch is energized to indicate battery condition; an icon 152 may be illuminated when display 110 indicates the time of day; an icon 154 and 156 may be illuminated when apparatus 100 is operating in the exercise mode and/or the user's heart rate is being displayed; and an icon 158 may be illuminated when apparatus 100 is operating in the exercise mode and the exercise duration is being recorded. Additionally, the user's heart rate may be displayed in a central region 160 of display 110 in the same display region displaying time when used as a conventional watch. Of course, the aforementioned examples of icons 150-160, each icon's function, depicted appearance, and/or respective position within display unit 110 are only illustrative of the possibilities. Fewer, additional, or alternative icons and/or icon locations are also possible.

Apparatus 100 may also comprise a communication status indicator 170. Status indicator 170 may comprise an outward facing light source viewable by the user when the watch is in use. In one aspect, the light source may comprise one or more lights, such as LEDs. In one embodiment, the light source may comprise a plurality of LEDs, each of a different color. In this manner, the color of the LED illuminated may convey additional information to a user regarding the communication status of apparatus 100. In another aspect, when apparatus 100 is in communication with another device via a suitable communication channel, such as Bluetooth communication, status indicator 170 may illuminate light of a first color. Where apparatus 100 is in communication with another device via some alternative communication channel, status indicator 170 may illuminate light of a second color. Alternatively, or additionally, status indicator 170 may illuminate light of another color when ongoing communication with another device is terminated and/or apparatus 100 ends or initiates an operational state. Again, these examples are only illustrative of the possibilities and status indicator 170 may illuminate one or more light sources corresponding to one or more colors to indicate or convey any suitable information to the user. For example, where apparatus 100 may be configured to monitor the user's heart rate, indicator 170 may illuminate light of a first color when the user's heart rate is in a first numerical range, illuminate light of a second color when the user's heart rate is in a second numerical range, and illuminate light of a third color when the user's heart rate is in a third numerical range. In this manner, a user may be able to detect his or her approximate heart rate at a glance, in instances when numerical heart rate information is not displayed at display unit 110, and/or through his or her peripheral vision.

Figure 2:
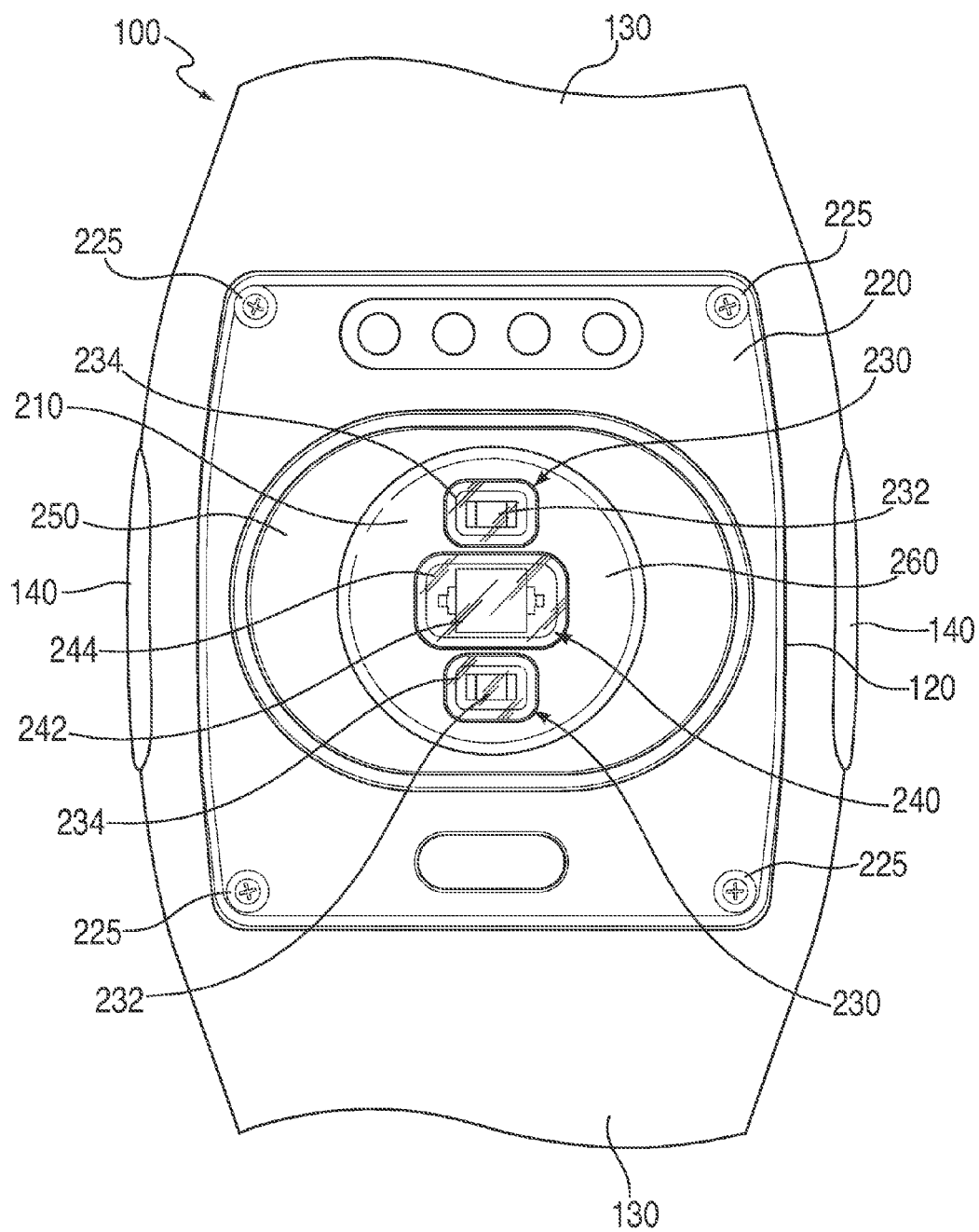
FIG. 2 depicts some aspects of an illustrative embodiment of an apparatus as described herein.

FIG. 2 depicts a rear view of an illustrative embodiment of apparatus 100. In one aspect, apparatus 100 may comprise a caseback 220. Caseback 220 may be secured to apparatus 100 using any suitable attachment system or method. For example, caseback 220 may be secured to apparatus 100 by one or more screws 225 or some other suitable attachment mechanism including, but not limited to, mating recesses and protrusions, a compression fitting, and/or an epoxy/glue.

Caseback 220 may further comprise one or more optical sensors 210 as described herein. Specifically, optical sensor 210 may comprise one or more light sources 230. As depicted in FIG. 2, the optical sensor may comprise two light sources 230 that are spaced apart from one another. Alternative embodiments may comprise fewer or additional light sources.

In the depicted arrangement, each light source 230 includes one or more LEDs 232 that may be contained in a respective lens 234. In that regard, it should be noted that lens 234 may not necessarily be the same as, nor replace, the integral lens of a conventional LED, which is configured to cause emitted light to pass from an end surface of the device. Located between and/or positioned adjacent or proximate to light sources 230 may be one or more optical detectors 240. In FIG. 2, optical detector 240 may comprise a photodiode 242 that may be contained by a lens 244. While the embodiment depicted in FIG. 2 comprises a single photodiode, alternative embodiments may comprise additional optical detectors and/or photodiodes positioned within caseback 220. Moreover, while apparatus 100 depicted in FIG. 2 may comprise a single optical sensor 210, alternative embodiments may comprise multiple optical sensors, each sensor comprising one or more light sources and/or optical detectors.

In some embodiments, lenses 234 and 244 may comprise a mineral glass or a plastic that exhibits a high degree of optical transmission at wavelengths of the optical energy emitted by LEDs 232. In alternative embodiments, lenses 234 and 244 may comprise some other suitable material. In some instances it may be possible to form lens 234 and 244 from material that imparts a filtering effect to the lenses. For example, ambient light that reaches photodiode 242 may be noise that can affect the operation and/or accuracy of a physiological parameter monitor. In embodiments in which LEDs 232 emit light sufficiently removed from the infrared region, apparatus 100 may comprise lenses that block a portion of incident infrared energy to thereby decrease the effect of any ambient light that may pass between caseback 220 and the user's tissue. In still further embodiments, one or more of lenses 234 and 244 may comprise an epoxy layer or encasement poured or placed into caseback 220 rather than a glass or plastic lens. Such an epoxy layer may be pre-formed or formed with a respective light source or optical detector positioned within caseback 220. For example, a liquid, semi-liquid, or gel-like epoxy may be poured over one or more of the light sources and/or photo detectors in caseback 220. The epoxy may then solidify into an epoxy layer that may completely or partially encase or encapsulate the one or more light sources and/or photo detectors. In other embodiments, the epoxy layer may be separated from the respective LED 232 or photodiode 242 by a barrier or by space.

In another aspect, caseback 220 may be configured such that the optical sensor may be in contact or urged firmly against the skin when apparatus 100 is worn by a user. In that regard, caseback 220 may include a raised portion 250 that may project inwardly from the surface of caseback 220. In a further embodiment, located in raised portion 250 may be a further raised portion 260. The raised and further raised portions may serve to adequately urge the optical sensor against the user's skin. In some embodiments, the surface of LED lenses 234 and optical detector lens 244 may be substantially flush with or extend slightly above the surface of the further raised portion 260. Of course, in other embodiments, caseback 220 may comprise only one of raised portion 250 and further raised portion 260. In further embodiments, caseback 220 may not comprise either of raised portion 250 or further raised portion 260. Alternatively, caseback 220 may comprise additional raised portions. Moreover, while FIG. 2 depicts raised portion 250 as a substantially elliptical region and further raised portion 250 as a substantially circular raised portion, other suitable shapes of the raised portions are possible and the depicted embodiments should not be construed to limit the possibilities.

In a further aspect, how far one or both of raised portion 250 and further raised portion 260 may project inwardly from caseback 220 may be fixed and predetermined. Alternatively, how far one or both of raised portion 250 and further raised portion 260 may project inwardly from caseback 220 may be adjustable so as to selectively achieve a desired pressure or level of contact between the optical sensor and the user's skin. In one embodiment, how far one or both of raised portion 250 and further raised portion 260 may inwardly project from caseback 220 may be adjusted manually through user manipulation of apparatus 100. In other embodiments, the height or inward projection of one or both of raised portion 250 and further raised portion 260 may be automatedly adjusted, prior to or during use, to a predetermined projection height/distance or a predetermined level of contact with the user's skin. Manual and automated adjustment of raised portion 250 and further raised portion 260 are described in more detail below with respect to FIGS. 5-9.

Figure 3A:
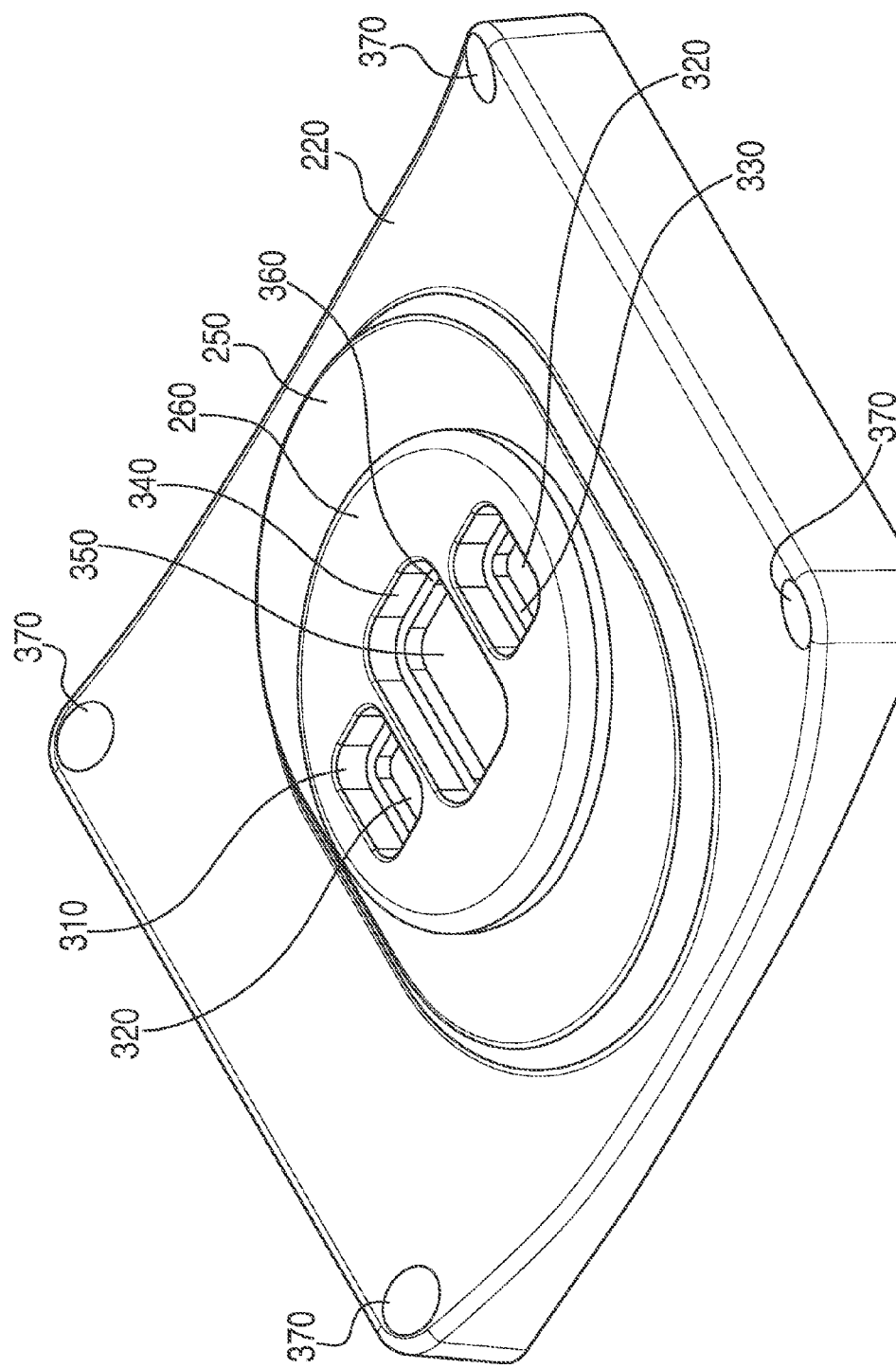
FIG. 3A depicts some aspects of an illustrative embodiment of an apparatus as described herein.

FIG. 3A depicts an illustrative embodiment of an inner surface of caseback 220, i.e., a surface closest to a targeted area of a user's body when apparatus 100 is in use, prior to the installation of light sources 230 (comprising, for example, LEDs 232 and lenses 234) and optical detector 240 (comprising, for example, photodiode 242 and lens 244). In one aspect, the inner surface of caseback 220 may comprise one or more recesses 310. Recesses 310 may extend outwardly toward an outer surface of caseback 220 for receiving lenses 234. The interior of each recess 310 may be shaped to substantially correspond with the exterior configuration of a lens 234. An opening 320 may be located at the bottom of each recess 310 for receiving an LED 232. Each opening 320 may be smaller than the cross-sectional area of the associated recess 310 so that a radially-inward extending ledge 330 may be formed around the lower periphery of the recess 310. When an LED lens 234 is inserted in recess 310, the bottom of the lens may come into abutment with ledge 330 and the inner face of the lens (i.e., the face closest to the targeted area of the user when apparatus 100 is in use) may be flush with, or project slightly beyond, the inner surface of caseback 220. Alternatively, the inner face of the lens may be slightly below, or depressed in relation to, the inner surface of caseback 220.

In another aspect, the inner surface of caseback 220 may comprise a recess 340. Recess 340, similar to recesses 310, may extend outwardly toward an outer surface of caseback 220 for receiving optical detector lens 244. In one embodiment, the configuration of recess 340 may correspond to that of recesses 310 in that the interior wall of recess 340 may be configured to substantially correspond with the exterior configuration of optical detector lens 244. An opening 350 may be located at the bottom of recess 340 for receiving a photodiode 242. Opening 350 may be smaller than the cross-sectional area of recess 340 so that a radially-inward extending ledge 360 may be formed around the lower periphery of recess 340. When an optical detector lens 244 is inserted in recess 340, the bottom of the lens may come into abutment with the ledge and the inner face of the lens (i.e., the face closest to the targeted area of the user when apparatus 100 is in use) may be flush with, or project slightly beyond, the inner surface of caseback 220. Alternatively, the inner face of the lens may be slightly below, or depressed in relation to, the inner surface of the caseback.

In a further aspect, recesses 310 and 340 may establish the position of LED lenses 234 relative to optical detector lens 244. This, in turn, may establish the distance between each LED 232 and photodiode 242. Further, recesses 310 and 340 may be positioned to ensure that sufficient light emitted by LEDs 232 may reach photodiode 242 after being reflected by the user's body, e.g., the blood flowing through the user's arteries and/or other vascular structure. Of course, the particular location of recesses 310 and 340 shown in FIG. 3 is only illustrative and any other suitable location of one or more of the recesses may be possible.

In another aspect, a portion of caseback 220 residing between recess 340 and each of recesses 310 may define respective barriers 520 (described in more detail below). Barriers 520 may serve to optically isolate photodiode 242 and each of LEDs 232, preventing light emitted from one or more LEDs 232 from reaching photodiode 242 without first being reflected from a targeted tissue area of a user placed in contact or near contact with the inner surface of caseback 220, raised portion 250, further raised portion 260, and/or lenses 234, 244. In one embodiment, barriers 520 may extend from the innermost surface of further raised portion 260 to a base portion of photodiode 242 and/or LEDs 232. In other embodiments, barriers 520 may extend from the innermost surface of further raised portion 260 to a circuit board upon which one or more of photodiode 242 and/or LEDs 232 may be mounted (as described below in more detail).

In a further aspect, the inner surface of caseback 220 may be contoured to substantially correspond with the wrist or forearm of the user. In one embodiment, openings 370 for threaded fasteners 225 (as shown in FIG. 2) may be located in caseback 220 to secure caseback 220 to casing 120 (shown in FIGS. 1 and 2).

Figure 3B:
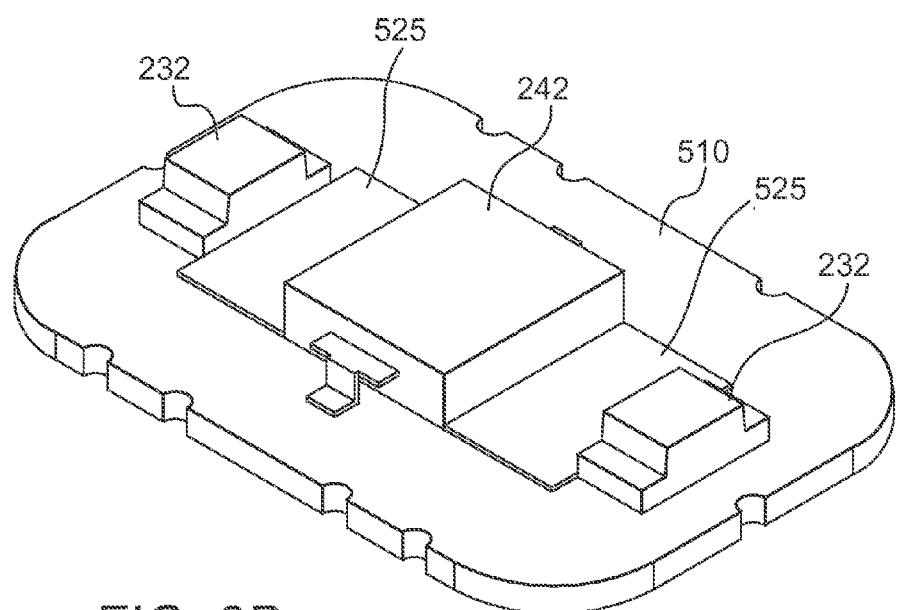
FIG. 3B depicts some aspects of an illustrative embodiment of an apparatus as described herein.

FIG. 3B depicts an arrangement for mounting LEDs 232 and photodiode 242. As depicted in FIG. 3B, LEDs 232 and photodiode 242 may be positioned relative to one another by means of a printed circuit board 510 that electrically connects the devices to other circuitry contained in apparatus 100 (such as the computing system depicted in FIG. 4). In one embodiment, a relatively thin strip of opaque, pliant material 525 (such as, but not limited to, a tape, a sponge-like polymer, or an epoxy) may extend between the edges of photodiode 242 and the adjacent edges of respective LEDs 232. As described relative to the assembled caseback (described in more detail below and depicted in FIGS. 5-10) opaque strips 525 may prevent light emitted by the LEDs 232 from travelling along the surface of printed circuit board 510 and reaching photodiode(s) 242.

Although FIG. 3B depicts LEDs 232 and photodiode 242 on a single circuit board, alternative embodiments comprising a plurality of circuit boards in communication with one another are also possible. In such embodiments, commands to and/or measurements from LEDs 232 and photodiode(s) 242 may be communicated via one or more wired or wireless communication channels.

Figure 3C:
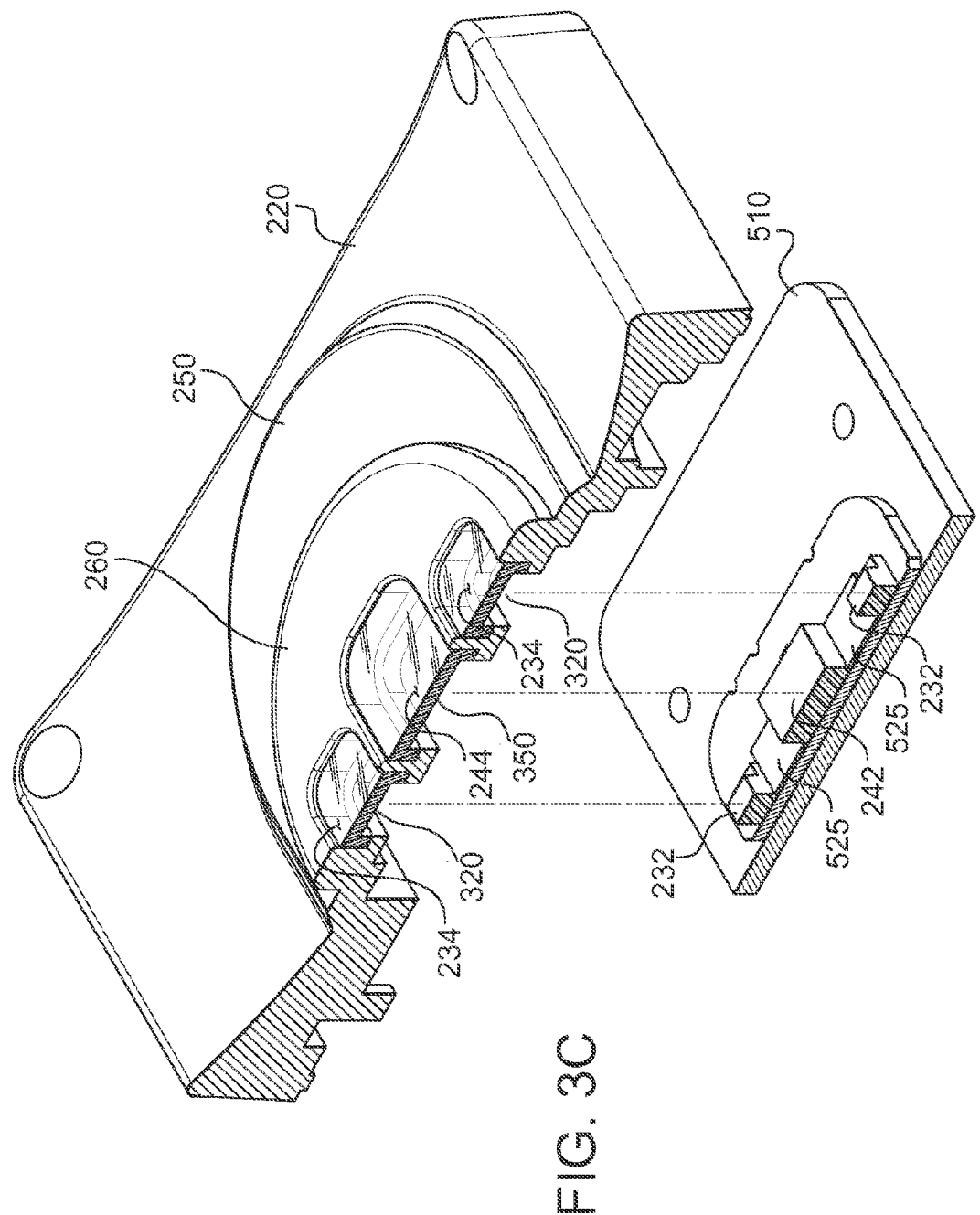
FIG. 3C depicts some aspects of an illustrative embodiment of an apparatus as described herein.
Figure 10:
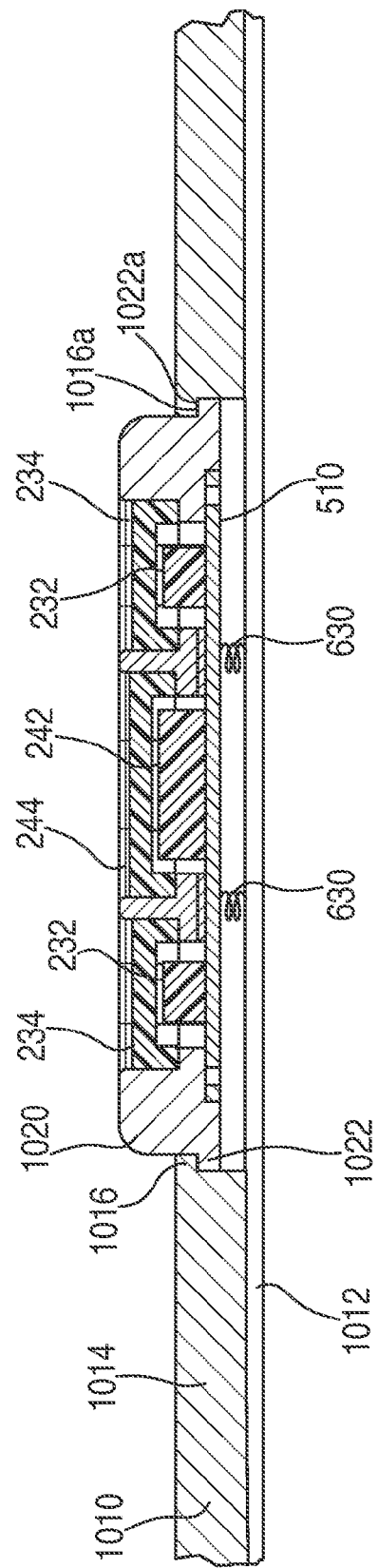
FIG. 10 depicts some aspects of an illustrative embodiment of an apparatus as described herein.

FIG. 3C is a partially cutaway view of caseback 220 and printed circuit board 510 that illustrates one possible manner in which the optical sensor may be incorporated in caseback 220 (or strap(s) 130 in embodiments that do not comprise a caseback, such as the embodiment depicted in FIG. 10). In FIG. 3C, LED lenses 234 may be inserted and sealed in recesses 310 of FIG. 3A. As previously indicated, the light-emitting surface of each lens 234 may be substantially flush with, or extend slightly above or below, the surface of further raised region 260.

In a like manner, optical detector lens 244 may be inserted and sealed in recess 340 of FIG. 3A. The light-receiving surface of lens 244 may be substantially flush with, or extend slightly above or below, the surface of further raised region 260. Various techniques can be used for bonding LED lenses 234 and optical detector lens 244 to caseback 220. For example, depending in part of the material being used for caseback 220 (or strap(s) 130), the lenses may be bonded in place by a curable adhesive, ultrasonic bonding or other techniques. In some applications, insert molding or cold-molding techniques may be employed. As indicated by phantom lines in FIG. 3C, LEDs 232 and photodiode(s) 242 may pass into openings 320 and 350, respectively, so that LEDs 232 may be at least partially contained or received by lenses 234 and photodiode(s) 242 may be at least partially contained or received by optical detector lens 244.

In alternative embodiments, rather than one or more of lenses 234 and 244 being inserted into recesses 310 and/or 340, one or more of the lenses may comprise an epoxy layer or encasement poured or placed into caseback 220. In such embodiments, circuit board 510 may be incorporated into caseback 220, as indicated by the phantom lines in FIG. 3C, such that LEDs 232 and photodiode(s) 242 may pass into openings 320 and 350, respectively, prior to pouring the epoxy for lenses 234 and 244. Once circuit board 510, LEDs 232, and photodiode(s) 242 are in place, the circuit board, LEDs, photodiode(s), caseback 220, and/or barriers 520 may serve as a form for the liquid or gel-like epoxy and define the shape of lenses 234 and 244 as the epoxy solidifies. The solidified may then comprise an epoxy lens or layer that may completely or partially encase or encapsulate the one or more light sources and/or photo detectors over which the epoxy was formed.

It should be noted that the caseback 200 depicted in FIG. 3C comprises a single piece in which the protrusion height of raised portion 250 and further raised portion 260 may be predetermined and fixed. In alternative embodiments described below, caseback 200 may comprise multiple cooperating components to facilitate the adjustment of the protrusion heights with respect to raised portion 250 and further raised portion 260.

Figure 4:
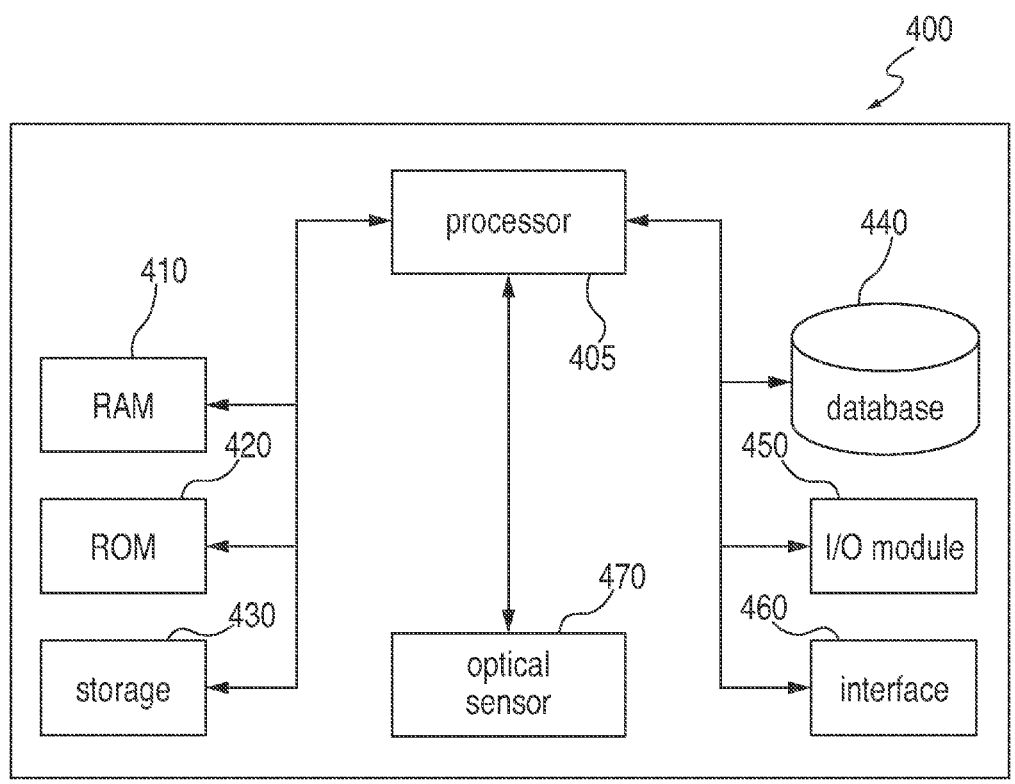
FIG. 4 depicts an illustrative embodiment of a computing system as described herein.

FIG. 4 depicts an illustrative processor-based computing system 400 representative of the type of computing system that may be present in or used in conjunction with any aspect of apparatus 100 comprising electronic circuitry. For example, processor-based computing system 400 may be used in conjunction with any one or more of transmitting signals to and from the optical sensor, sensing or detecting signals received at the optical sensor, processing received signals, and storing, transmitting, or displaying information. Computing system 400 is illustrative only and does not exclude the possibility of another processor- or controller-based system being used in or with any of the aforementioned aspects of apparatus 100.

In one aspect, system 400 may include one or more hardware and/or software components configured to execute software programs, such as software for storing, processing, and analyzing data. For example, system 400 may include one or more hardware components such as, for example, processor 405, a random access memory (RAM) module 410, a read-only memory (ROM) module 420, a storage system 430, a database 440, one or more input/output (I/O) modules 450, an interface module 460, and an optical sensor module 470. Alternatively and/or additionally, system 400 may include one or more software components such as, for example, a computer-readable medium including computer-executable instructions for performing methods consistent with certain disclosed embodiments. It is contemplated that one or more of the hardware components listed above may be implemented using software. For example, storage 430 may include a software partition associated with one or more other hardware components of system 400. System 400 may include additional, fewer, and/or different components than those listed above. It is understood that the components listed above are illustrative only and not intended to be limiting or exclude suitable alternatives or additional components.

Processor 405 may include one or more processors, each configured to execute instructions and process data to perform one or more functions associated with system 400. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 4, processor 405 may be communicatively coupled to RAM 410, ROM 420, storage 430, database 440, I/O module 450, interface module 460, and optical sensor module 470. Processor 405 may be configured to execute sequences of computer program instructions to perform various processes, which will be described in detail below. The computer program instructions may be loaded into RAM for execution by processor 405.

RAM 410 and ROM 420 may each include one or more devices for storing information associated with an operation of system 400 and/or processor 405. For example, ROM 420 may include a memory device configured to access and store information associated with system 400, including information for identifying, initializing, and monitoring the operation of one or more components and subsystems of system 400. RAM 410 may include a memory device for storing data associated with one or more operations of processor 405. For example, ROM 420 may load instructions into RAM 410 for execution by processor 405.

Storage 430 may include any type of storage device configured to store information that processor 405 may need to perform processes consistent with the disclosed embodiments.

Database 440 may include one or more software and/or hardware components that cooperate to store, organize, sort, filter, and/or arrange data used by system 400 and/or processor 405. For example, database 440 may include user profile information, historical physiological parameter information, predetermined menu/display options, and other user preferences. Alternatively, database 440 may store additional and/or different information.

I/O module 450 may include one or more components configured to communicate information with a user associated with system 400. For example, I/O module 450 may comprise one or more buttons, switches, or touchscreens to allow a user to input parameters associated with system 400. I/O module 450 may also include a display including a graphical user interface (GUI) and/or one or more light sources for outputting information to the user. I/O module 450 may also include one or more communication channels for connecting system 400 to one or more peripheral devices such as, for example, a desktop computer, a laptop, a tablet, a smart phone, a flash drive, or a printer, to allow a user to input data to or output data from system 400.

Interface 460 may include one or more components configured to transmit and receive data via a communication network, such as the Internet, a local area network, a workstation peer-to-peer network, a direct link network, a wireless network, or any other suitable communication channel. For example, interface 460 may include one or more modulators, demodulators, multiplexers, demultiplexers, network communication devices, wireless devices, antennas, modems, and any other type of device configured to enable data communication via a communication network.

Optical sensor module 470, described in more detail above, may comprise optical sensor 210 and related circuitry. In one embodiment, in addition to transmitting and receiving information from optical sensor 210, optical sensor module 470 may be configured to receive signals from, or output signals to, other components or modules of system 400.

FIG. 5A depicts a cross-sectional view of one embodiment of apparatus 100 comprising caseback 220 and optical sensor 210. In one embodiment, apparatus 100 may comprise a first circuit board 510. First circuit board 510 may support, among other things, optical sensor 210, including one or more light sources 230 (comprising, for example, LEDs 232 and lenses 234) and/or optical detectors 240 (comprising, for example, photodiode 242 and lens 244). Circuit board 510 may also serve to electrically connect one or more components of optical sensor 210 to other devices and/or circuitry within apparatus 100. As depicted, one or more components of optical sensor 210 may be located on a single circuit board 510. Alternative embodiments, some of which are described below, may comprise a plurality of circuit boards in communication with one another and/or each comprising one or more discrete components of optical sensor 210. In such embodiments where circuit board 510 may comprise a plurality of discrete circuit boards, information sent to and received from LEDs 232 and photodiode 242 may be communicated via one or more wired, wireless, or electrical contact communication channels.

In another aspect, one or more placement posts 515, located within apparatus 100 and extending through or about circuit board 510 may maintain circuit board 510 in a fixed position relative to all or a portion of caseback 220. In one embodiment, placement posts 515 may be cylindrical in shape and may be located so as to form a rectangular pattern extending vertically within caseback 220. In alternative embodiments, placement posts 515 may exhibit some other suitable shape and/or may be positioned in another arrangement for ensuring proper positioning of circuit board 510.

In an embodiment where one or more components of optical sensor 210 are located on circuit board 510, proper placement of circuit board 510 within caseback 220 may, in turn, ensure proper positioning of one or more optical sensors components, e.g., LEDs 232 and/or photodiode 242, with respect to caseback 220 and/or corresponding LED lenses 234 and/or optical detector lens 244.

In a further aspect, FIG. 5A depicts one possible manner in which optical sensor 210 may be incorporated in caseback 220. In one embodiment, LED lenses 234 may be inserted and sealed in recesses 310 (shown in FIG. 3). As previously indicated, the lower surface of each lens 234 may be in abutment with ledge 330 and the light-emitting surface of each lens 234 may be substantially flush with, or extend slightly above or below, the surface of further raised portion 260.

In a similar manner, optical detector lens 244 may be inserted and sealed in recess 340 (shown in FIG. 3). In one embodiment, the lower surface of lens 244 may be in abutment with ledge 360 and the light-receiving surface of lens 244 may be substantially flush with, or extend slightly above or below, the surface of further raised portion 260.

A number of techniques may be used for bonding LED lenses 234 and optical detector lens 244 to caseback 220. For example, depending in part on the material used for caseback 220 and the respective lenses, the lenses may be bonded in place by a curable adhesive, ultrasonic bonding, or other techniques. In some applications, insert molding or cold-molding techniques may be employed.

In one aspect, LEDs 232 and photodiode 242 may pass into openings 320 and 350, respectively, so that LEDs 232 may be contained by lenses 234 and photodiode 242 may be contained by optical detector lens 244. In one embodiment, openings 320 for receiving LEDs 232 may be smaller than the recesses 310 for receiving LED lenses 234. Similarly, opening 350 for receiving photodiode 242 may be smaller than recess 340 for receiving the optical detector lens 244. In this manner, each combination of LED 232 and LED lens 234 may be physically and optically separated from photodiode 242 and optical detector lens 244 by a respective barrier 520 that may extend downwardly from further raised portion 260 of caseback 220 to the base of LEDs 232 or photodiode 242, or the upper surface of circuit board 510.

In a further embodiment, each barrier 520 may comprise an inverted T-shaped barrier. As is shown in FIG. 5A, the radially-inner edges of LED lenses 234 may be separated from the radially-outer edges of optical detector lens 244 by an upwardly extending leg of T-shaped barrier 520 and the radially-inner edges of LEDs 232 may be separated from the radially-outer edges of photodiode 242 by a laterally extending lower leg of the T-shaped barrier 520. Of course, the T-shaped barrier is only one illustrative embodiment of barrier 520 and, in alternative embodiments, barrier 520 may be any suitable shape for isolating LEDs 232 and photodiode 242.

In still a further embodiment, a relatively thin strip of opaque pliant material 525 (such as, but not limited to, a tape or a sponge-like polymer) may be in contact with, press against, and/or extend between the lower surface of barrier 520 and the upper surface of circuit board 510. In another embodiment, opaque strips 525 may be in contact with, press against, and/or extend between the radially outer edges of photodiode 242 and the adjacent edges of LEDs 234.

Opaque strips 525 may prevent light emitted by LEDs 232 from travelling along the surface of circuit board 510 and reaching photodiode 242, i.e., ensure that light emitted by LEDs 232 does not reach photodiode 242 without being reflected by a targeted region of the user. Alternative embodiments may comprise a non-transparent epoxy or some other material in addition to, or instead of, opaque strips 525.

In another aspect of the embodiment depicted at FIG. 5A, first circuit board 510 may be positioned above and/or spaced apart from an upper surface of a second circuit board 530. Circuit board 530 may include circuitry (not shown) for performing one or more functions of apparatus 100, including but not limited to, detecting and displaying a user's heart rate, the time of day and other information. In other embodiments, first circuit board 510 and second circuit board 530 may be a single circuit board. For example, a single flexible circuit board may be flexed or bent into a substantially "U shape" such that each opposing extension of the "U" may comprise flexible circuit board 510 and 530, respectively.

One or more placement posts 535, located within apparatus 100 and extending through or about circuit board 530 may maintain circuit board 530 in a fixed position relative to all or a portion of apparatus 100. In one embodiment, placement posts 535 may be cylindrical in shape and may be located so as to form a rectangular pattern extending vertically within apparatus 100. In alternative embodiments, placement posts 535 may exhibit some other suitable shape and/or may be positioned in another arrangement for ensuring proper positioning of circuit board 530. Proper placement of circuit board 530 within apparatus 100 may, in turn, ensure proper positioning of circuit board 530 with respect to circuit board 510 and/or ensure reliable communication between circuit board 530 and circuit board 510.

In a further aspect, circuit board 510 and circuit board 530 may be in wired, wireless, or electrical contact with one another to facilitate the exchange of signals/information between them. In one embodiment, circuit board 510 may comprise one or more downwardly extending pogo pins 540 mounted to the lower surface of circuit board 510 and extending so as to contact the upper surface of circuit board 530. In another embodiment, circuit board 530 may comprise one or more upwardly extending pogo pins 540 mounted to the upper surface of circuit board 530 and extending so as to contact the lower surface of circuit board 510. In alternative embodiments, one or more electrical communication channels may be established between circuit boards 510 and 530 using some other means, such as one or more flexible circuits or tapes comprising embedded wiring. In further embodiments, any suitable connection for establishing electrical communication between circuit boards 510 and 530 may be used.

In another aspect of the embodiment depicted in FIG. 5A, raised portion 250 and further raised portion 260 may comprise discrete components of apparatus 100. In one embodiment, apparatus 100 may be configured to allow for the inward and outward movement of further raised portion 260 with respect to raised portion 250. In such embodiments where further raised portion 260 may house optical sensor 210 and its various components, a degree of contact and/or pressure established between the components of optical sensor 210 and the user may be adjusted.

In a further embodiment, further raised portion 260 may be threadedly mated with raised portion 250 such that the rotation of further raised portion 260 with respect to raised portion 250 in a first direction (e.g., counter-clockwise) may result in the movement of further raised portion 260 (and optical sensor 210) toward the user, i.e., achieves greater contact or pressure between sensor 210 and the targeted area of the user's body. Conversely, rotation of further raised portion 260 with respect to raised portion 250 in an opposite direction (e.g., clockwise) may result in the movement of further raised portion 260 (and optical sensor 210) away from the user, i.e., reduced contact or pressure between sensor 210 and the targeted area of the user's body.

In a further aspect, optical sensor 210, including one or more of its components, and/or circuit board 510 may rotate in conjunction with further raised portion 260. In one embodiment, the separation between circuit boards 510 and 530 and/or the presence of pogo pins 540 may facilitate continuous electrical contact between circuit boards 510 and 530 during such rotation, i.e., the height of pogo pins 540 may correspondingly increase or decrease as the distance between circuit boards 510 and 530 increase or decrease.

Moreover, in an embodiment in which one or more pogo pins 540 may be mounted to the lower surface of circuit board 510 and extend to a point of contact with the upper surface of circuit board 530, circuit board 530 may comprise circular or annular contact strips corresponding to each pogo pin to ensure that each pogo pin is in constant electrical contact with circuit board 530, regardless of the rotational positioning of sensor 210 and/or circuit board 510. An embodiment of circuit board 530 comprising a contact region 542a and annular contact strips 542b and 542c, each corresponding to the location of a respective pogo pin 540 (depicted in FIG. 5A) is depicted in FIG. 5B. Of course, such an embodiment is only illustrative of one possibility. Other embodiments may comprise pogo pins 540 mounted to the upper surface of circuit board 530 and extending to a point of contact with the lower surface of circuit board 510. In such an embodiment, the aforementioned annular contact strips may reside on the lower surface of circuit board 510 rather than the upper surface of circuit board 530. In alternative embodiments, rather than pogo pins, apparatus 100 may comprise some other suitable electrical connections between circuit boards 510 and 530.

In another aspect, the rotation of further raised portion 260 (and/or optical sensor 210) relative to raised portion 250 may be performed manually by the user or in an automated fashion. In one embodiment, the user can physically manipulate further raised portion 260 in order to rotate it with respect to raised portion 250 and/or the remainder of caseback 220. In such an embodiment, further raised portion 260 may comprise tactile ridges or a textured surface to allow the user to adequately grip the periphery of further raised portion 260. Such a textured surface may be advantageous when apparatus 100 is used in the course of physical exercise and may become wet from the user's perspiration. Alternatively, further raised portion 260 may be rotated using a mating tool. For instance, further raised portion 260 may comprise a depression (not shown) configured to mate with an instrument the user may insert into the depression to facilitate rotation of further raised portion 260. Of course, these example are only illustrative of the possibilities and any suitable mechanism for performing manual rotation of further raised portion 260 with respect to raise region 250 and/or the remainder of caseback 220 may be used.

Regardless of the mechanism, in such embodiments, a user may selectively determine the protrusion height of further raised portion 260, i.e., the distance from the inner surface of further raised portion 260 (the surface in contact with the targeted area of the user's skin) and the inner surface of raised portion 250. The greater the protrusion height, the greater the contact or pressure may be between sensor 210 and the targeted area of the user's body. The less the protrusion height, the less the contact or pressure may be between sensor 210 and the targeted area of the user's body. Moreover, because the size and shape of users' wrists, arms, or other extremities may vary, one subset of users may find it beneficial for apparatus 100 to exhibit a relatively low protrusion height of further raised portion 260, while another subset of users may find it advantageous for apparatus 100 to exhibit a relatively high protrusion height of further raised portion 260. It should also be mentioned that although the depicted embodiments describe raising or lowering the protrusion height of further raised portion 260 with respect to raised portion 250, this disclosure should be understood to encompass designs that comprise only a single raised portion, the protrusion height of which may be varied with respect to the inner surface of caseback 220. Every embodiment need not comprise both a raised portion and a further raised portion.

In other embodiments, the rotation of further raised portion 260 with respect to raised portion 250 and/or caseback 220 may be automated. In such an embodiment, a motor may be coupled to further raised portion so as to achieve the aforementioned rotation. This may be achieved, among other ways, using one or more gears and/or shafts/axles. Where the rotating action may be automated, a user may predetermine a desired level of contact of pressure to be achieved between sensor 210 and the targeted area of the user's body. Before or after securing apparatus to the targeted area using bands 130, the motor may activate and cause further raised portion 260 to rotate toward or away from the user's body. The motor may continue to rotate further raised portion until a level of contact or pressure with the targeted area of the user's body is too great for further raised portion 260 to advance further. Alternatively, the motor may rotate further raised portion to a predetermined protrusion height that may or may not correspond with an estimate level of contact or pressure. In still further embodiments, the inner surface of further raised portion 260 or optical sensor 210 may comprise a pressure sensor that may be positioned adjacent the targeted area of the user's body and signals the motor to cease rotation when a desired or predetermined level of contact or pressure is achieved between optical sensor 210 and the targeted area.

Additionally, the initiation or activation of the motor and, consequently, the rotation of further raised portion 260 may be controlled by the user or automated. For instance, the user may initiate the motor through manipulation of one or more of switches 140 (shown in FIG. 1). Alternatively, activation of the motor may occur automatically when apparatus 100 enters into a physiological parameter monitoring mode, e.g., a heart rate monitoring mode. The user may also have the ability to stop the motor and/or the rotation of further raised portion 260 using similar means or by exiting a physiological parameter monitoring mode.

Moreover, the user may be afforded an opportunity to select a predetermined protrusion height of further raised portion 260 or a level of contact or pressure between optical sensor 210 and the targeted area of the user's body through the manipulation of one or more inputs of apparatus 100 (e.g., one or more switches 140) in conjunction with one or more menus that may be incorporated into the user interface of apparatus 100 (e.g., display 110 or a remote display device).

Figure 6:
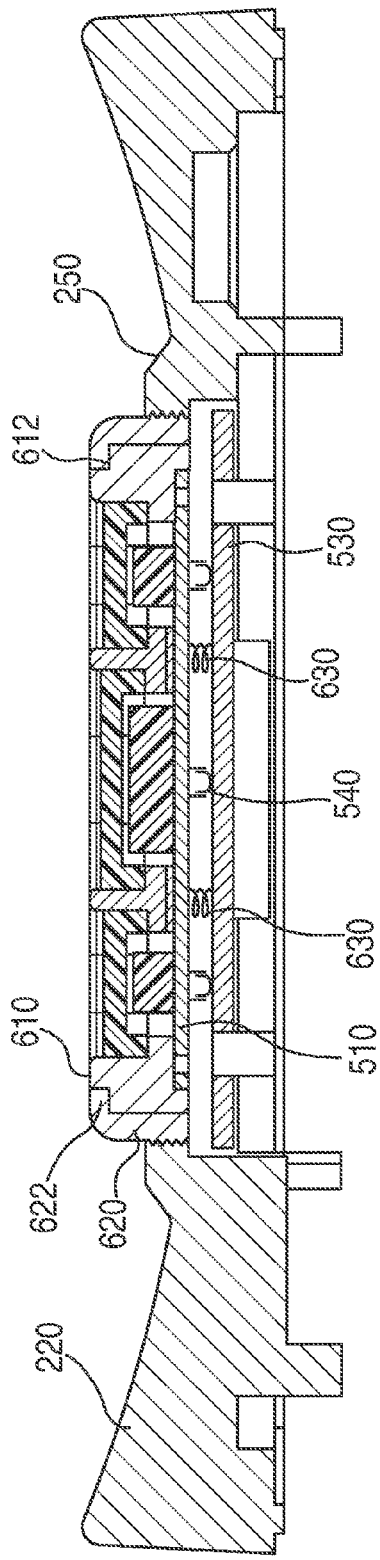
FIG. 6 depicts some aspects of an illustrative embodiment of an apparatus as described herein.

FIG. 6 depicts a cross-sectional view of another embodiment of apparatus 100. In one aspect, the embodiment depicted in FIG. 6 may be substantially similar to the embodiment depicted in FIG. 5A. In the embodiment of FIG. 6, however, further raised portion 260 may be comprised of a central portion 610 and an adjustment ring 620. In particular, adjustment ring 620 may comprise a radially outer ring or annular body encircling or surrounding central portion 610.

In another aspect, a radially inner surface of adjustment ring 620 may be in contact with a radially outer surface of central portion 610. The radially inner surface of adjustment ring 620 and the radially outer surface of central portion 610 may be substantially smooth to allow central portion 610 to slide or translate with respect to adjustment ring 620. In the embodiment of FIG. 6, central portion 610 and adjustment ring 620 may enjoy at least two degrees of freedom with respect to one another, i.e., they may slide or translate with respect to one another along their common interface (toward and away from the targeted area of the user) and they may rotate with respect to one another.

In a further aspect, adjustment ring 620 may comprise a lip extending radially inward and located at the inner surface of further raised portion 260, i.e., the surface of further raised portion 260 closest or in contact with the targeted area of the user's body. Central portion 610, on the other hand, may comprise a depression or recess 612 around its perimeter and located adjacent or proximate to the inner surface of further raised portion 260. In this manner, and as shown in FIG. 6, lip 622 of adjustment ring 620 may be positioned within recess 612 of central portion 610.

In another aspect, one or more resilient members 630 may be positioned between circuit board 510 and circuit board 530. Resilient members 630 may, among other things, serve to urge circuit board 510, optical sensor 210, and/or central portion 610 of further raised portion 260 toward the targeted area of the user's body. Central portion 610 (as well as circuit board 510 and optical sensor 210) may be retained in apparatus 100, however, by lip 622 of adjustment ring 620 of further raised portion 260.

In one embodiment, one or more resilient members 630 may be a spring. In further embodiments, one or more resilient members may be a compression spring, constant spring, variable spring, cantilever spring, helical spring, leaf spring, or some other suitable spring. In such embodiments, the one or more springs may exhibit a predetermined spring constant (k) suitable for use in apparatus 100 and/or affording a proper amount of resistance or contact pressure between lip 622 of adjustment ring 620 and recess 612 of central portion 610 to ensure that further raised portion 260/optical sensor 210 may advance toward the targeted area of the user's body as adjustment ring 620 advances toward the targeted area.

Similar to the embodiment depicted in FIG. 5A, the radially outer surface of adjustment ring 620 may be threadedly mated with raised portion 250 such that the rotation of adjustment ring 620 with respect to raised portion 250 in a first direction (e.g., counter-clockwise) may result in the movement of adjustment ring 620 toward the user. Conversely, rotation of adjustment ring 620 with respect to raised portion 250 in an opposite direction (e.g., clockwise) may result in the movement of adjustment ring 620 away from the user. Because central portion 610 (as well as one or both of optical sensor 210 and circuit board 510) may be spring urged against lip 622 of adjustment ring 620 by one or more resilient members 630, as adjustment ring 620 moves toward the user (i.e., rotates in a first direction), central portion 610 and optical sensor 210 may be urged toward the user. Thus, as adjustment ring 620 moves toward the user, greater contact or pressure between sensor 210 and the targeted area of the user's body may be achieved. Conversely, as adjustment ring 620 moves away from the user (i.e., rotates in a second direction), central portion 610 and optical sensor 210 may be depressed (via lip 622) against the action of resilient members 630. Therefore, as adjustment ring 620 moves away from the user, less contact or pressure between sensor 210 and the targeted area of the user's body may result.

As described above with respect to FIG. 5A, the rotation of adjustment ring 620 with respect to caseback 220 or raised portion 250 may be performed manually or may be automated. In either case, optical sensor 210 (and/or central portion 610 and circuit board 510) may not need to rotate as adjustment ring 620 rotates. Thus, the annular contact rings of circuit board 530 depicted in FIG. 5B may not be necessary. Rather, a connection point between circuit board 530 and one or more pogo pins 540 may remain fixed. Of course, rather than pogo pins, other embodiments may comprise a flexible circuit or tape to facilitate communication between circuit boards 510 and 530. In still further embodiments, any connection type that allows for dynamic separation or spacing between circuit boards 510 and 530 may be implemented.

Figure 7:
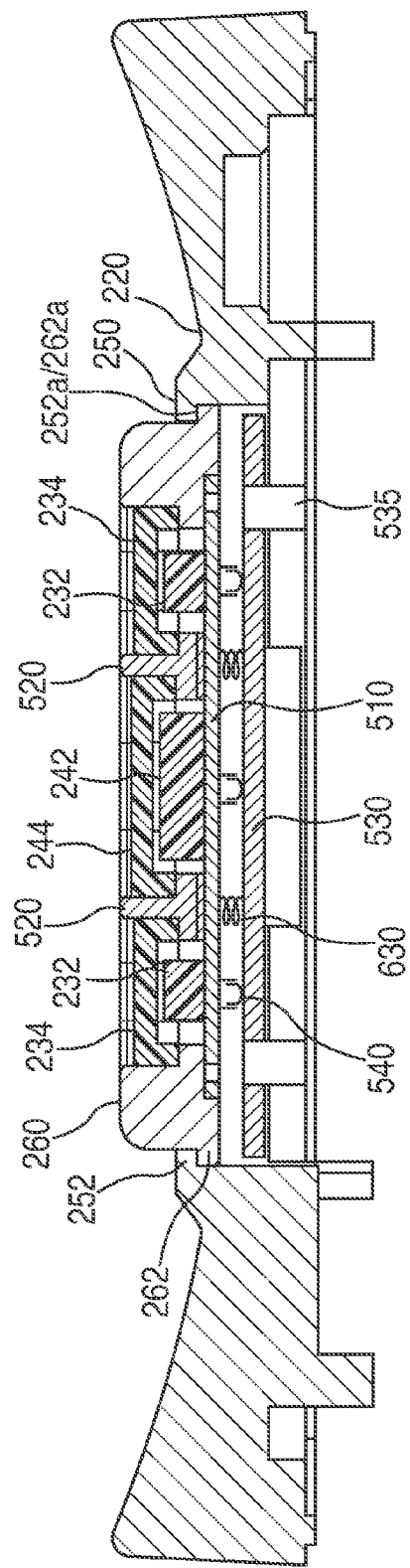
FIG. 7 depicts some aspects of an illustrative embodiment of an apparatus as described herein.

FIG. 7 depicts a cross-sectional view of yet another embodiment of apparatus 100. In one aspect, the embodiment depicted in FIG. 7 may be substantially similar to the embodiment depicted in FIG. 5A. In the embodiment of FIG. 7, however, the interface between further raised portion 260 and raised portion 250 may not be threaded. Rather, where further raised portion 260 and raised portion 250 may be in contact, the surfaces of further raised portion 260 and raised portion 250 may be substantially smooth to allow further raised portion 260 to slide or translate in a direction toward or away from the targeted area of the user with respect to raised portion 250.

In one aspect, further raised portion 260 may comprise a lip 262 at the outer surface of further raised portion 260, i.e., the surface closest to circuit board 510 and farthest from the targeted area of the user. In one embodiment, lip 262 may extend radially outward from further raised portion 260 so as to create an abutment surface 262a at the innermost (closest to the targeted area) surface of lip 262.

In another aspect, raised portion 250 may comprise an opposing lip 252 at the inner surface of raised portion 250, i.e., the surface positioned closest to the targeted area of the user. Opposing lip 252 may extend radially inward from raised portion 250 so as to create an opposing abutment surface 252a at the outermost (farthest from the targeted area) surface of lip 252.

In a further aspect, and similar to the embodiment depicted in FIG. 6, one or more resilient members 630 may be positioned between circuit board 510 and circuit board 530. Resilient members 630 may, among other things, serve to urge circuit board 510, optical sensor 210, and/or further raised portion 260 toward the targeted area of the user's body. In one embodiment, one or more resilient members 630 may be a spring. In further embodiments, one or more resilient members may be a compression spring, constant spring, variable spring, cantilever spring, helical spring, leaf spring, or some other suitable spring. In such embodiments, the one or more springs may exhibit a predetermined spring constant (k) suitable for use in apparatus 100 and/or affording a proper amount of resistance or contact pressure between further raised portion 260/optical sensor 210 and the targeted area of the user's body.

The one or more resilient members may urge further raised portion 260 (and/or circuit board 510 and optical sensor 210) inward toward the targeted area. Further raised portion 260 (and/or circuit board 510 and optical sensor 210) may be retained in apparatus 100, however, by an engagement or abutment of lip 262 of further raised portion 260 with opposing lip 252 of raised portion 250.

In this manner, when apparatus 100 is not being worn by a user and no pressure is applied to the inner surface of further raised portion 260 by the targeted area of the user, further raised portion 260 may be spring urged away from circuit board 530 and retained in an inwardly-urged position by the engagement or contact between lip 262 of further raised portion 260 and opposing lip 252 of raised portion 250. When apparatus 100 is in use, however, and the inner surface of further raised portion 260 may be in contact with (or pressed against) the targeted area of the user's body, the contact or pressure between the targeted area of the user and further raised portion 260 may compress one or more resilient members 630. This compression may, in turn, result in an increasing level of contact or pressure between optical sensor 210 (at the inner surface of further raised portion 260) and the targeted area of the user's body.

Among the advantages to the embodiment depicted in FIG. 7, the adjustment of the protrusion height of further raised portion 260 relative to the remainder of caseback 220 or raised portion 250 may be automated, i.e., requires little or no intervention by the user apart from the user's securing of apparatus 100 to the targeted area of the user via, for example, bands 130. For example, as the user secures apparatus 100 to the targeted area of the user, further raised portion 260 and/or optical sensor 210 may come into contact with the user's body and compress resilient members 630. Nonetheless, the resilient members spring urging of further raised portion 260 toward the user may result in optical sensor 210 maintaining an adequate level of contact or pressure against the targeted area.

Figure 8:
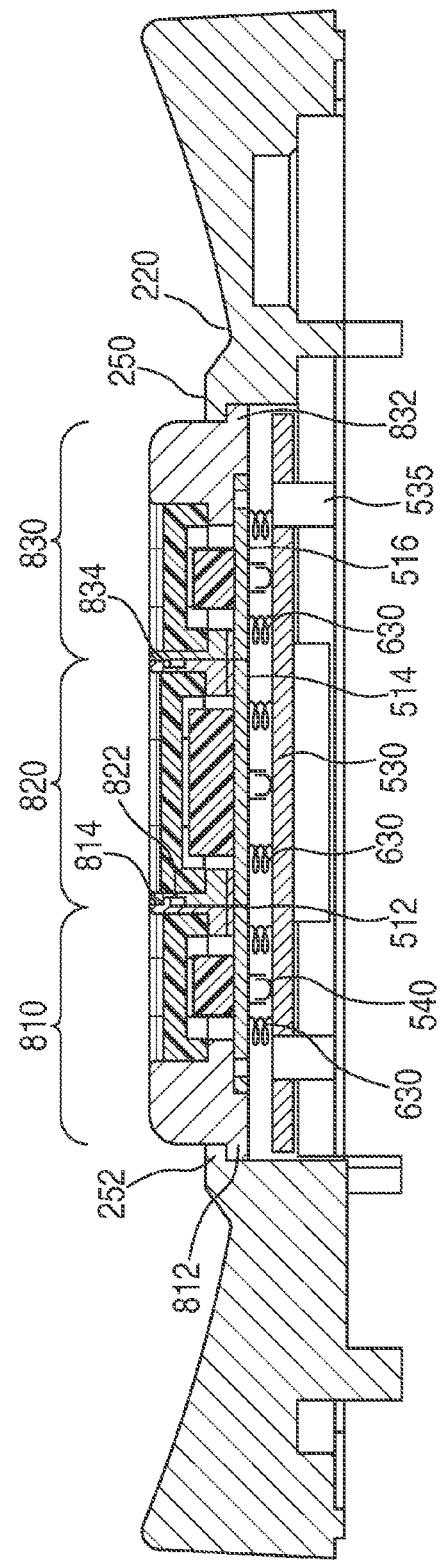
FIG. 8 depicts some aspects of an illustrative embodiment of an apparatus as described herein.

FIG. 8 depicts a cross-sectional view of another embodiment of apparatus 100. In one aspect, the embodiment depicted in FIG. 8 may be substantially similar to the embodiment depicted in FIG. 7. In one aspect, however, the embodiment depicted in FIG. 8 may comprise an optical sensor 210 comprising three discrete components: a pair of lateral components 810, 830 and an intermediate component 820. In one embodiment, lateral component 810 may comprise a light source 230, e.g., an LED 232 and an LED lens 234, lateral component 830 may similarly comprise a light source 230, e.g., an LED 232 and an LED lens 234, and intermediate component 820 may comprise an optical detector 240, e.g., a photodiode 242 and photodiode lens 244. In a further embodiment, each of the discrete components of optical sensor 210 may move toward or away from the targeted area of the user's body independent of the other components. In this manner, optical sensor 210 may contour to a unique user's body and each discrete component of the optical sensor may be more reliably secured against the targeted area.

In another aspect, circuit board 510, like optical sensor 210, may be comprised of a plurality of circuit boards. As shown, circuit board 510 may comprise sub-boards 512, 514, and 516. Each of sub-boards 512, 514, and 516 may be substantially similar to circuit board 510 of other embodiments. Moreover, sub-boards 512, 514, and 516 may be associated with one or more constituents of lateral component 810 (e.g., an LED 232 and an LED lens 234), intermediate component 820 (e.g., a photodiode 242 and photodiode lens 244), and lateral component 830 (e.g., an LED 232 and an LED lens 234), respectively.

In another aspect, sub-boards 512, 514, and 516 may be positioned above circuit board 530 and substantially adjacent to one another. In some embodiments, sub-boards 512, 514, and 516 may be in wired, wireless, or other electrical communication with one another. In other embodiments, sub-boards 512, 514, and 516 may also or alternatively be in wired, wireless, or other electrical communication with circuit board 530.

In another aspect, each sub-board may be supported with respect to circuit board 530 by one or more resilient members 630. In one embodiment, resilient members 630 may be positioned between circuit board 530 and a respective sub-board. In this manner, each of sub-boards 512, 514, and 516 may be permitted to move toward and away from the targeted area of the user's body, independent of the other sub-boards. Similar to the embodiments depicted in FIGS. 5-7, a plurality of respective pogo pins may serve to transmit information from the discrete components of optical sensor 210 and its associated sub-board to other components of apparatus 100 (e.g., circuit board 530) even as the spacing between circuit board 530 and the sub-boards vary in accordance with the level of contact or pressure exerted on the inner surface of optical sensor 210 or further raised portion 260.

In a further aspect, resilient members 630 may, among other things, serve to urge each sub-board (as well as a respective, discrete component of further raised portion 260) toward the targeted area of the user's body. Lateral components 810, 830 and intermediate component 820 may be retained in apparatus 100 against the force of resilient members 630 through a plurality of abutting and/or interlocking lips or recesses.

In one aspect, the radially outer surface of lateral components 810 and 830 may each comprise a lip 812 and 832, respectively. Lips 812 and 832 may be substantially similar to lip 262 depicted in FIG. 7. Similar to the embodiment depicted in FIG. 7, lips 812 and 832 may engage or abut lip 252 of raised portion 250 as lateral components 810 and 830 are urged away from circuit board 530 and no contact or pressure is applied to the surface of optical sensor 210 facing toward the targeted area of the user.

In another aspect, the radially inner surface of lateral components 810 and 830 may comprise a lip 814, 834, respectively. Lips 814 and 834 may, in some embodiments, extend from the radially inner surface of its respective lateral component and extend toward intermediate component 820. In a further embodiment, the radially outer surface of intermediate component 820 may comprise a recess 822 into which lips 814 and/or 834 may extend. In this manner, discrete components 810, 820, and 830 may be retained within apparatus 100 against the force of one or more resilient members acting on one or more sub-boards 512, 514, and 516. Of course, in alternative embodiments, the radially inner surface of lateral components 810 and 830 may comprise recesses and the radially outer surface of intermediate component 820 may comprise a lip extending radially outward into the recesses.

As described with respect to other embodiments, one or more resilient members 630 may be a spring. In further embodiments, one or more resilient members may be a compression spring, constant spring, variable spring, cantilever spring, helical spring, leaf spring, or some other suitable spring. In such embodiments, the one or more springs may exhibit a predetermined spring constant (k) suitable for use in apparatus 100 and/or affording a proper amount of resistance or contact pressure between each discrete component of optical sensor 210 and the targeted area of the user's body.

In some embodiments, the spring constant (k) for the resilient members associated with each sub-board may vary. For example, resilient members having a higher spring constant (i.e., stiffer springs offering greater resistance to depression) may be associated with one or both of sub-boards/lateral portions 512/810 and 516/830 while resilient members having a lower spring constant (i.e., weaker springs offering less resistance to depression) may be associated with sub-board/intermediate portion 514/820. Of course, other embodiments are also possible, including embodiments in which the intermediate portion may be associated with a stiffer spring and one or more lateral components may be associated with weaker springs.

When the embodiment of apparatus 100 depicted in FIG. 8 is not being worn by a user and/or no pressure is applied to the inner surface of optical sensor 210 or further raised portion 260 by the targeted area of the user, optical sensor 210 (including each of its discrete components) may be spring urged away from circuit board 530 and retained in an inwardly-urged position by the engagement or contact between lips 812, 832, and 252 at the radially outer surface of optical sensor 210 and the engagement or contact between lips 814, 834 and recess 822 at the interfaces between lateral components 810, 830 and intermediate component 820.

When the embodiment of apparatus 100 depicted in FIG. 8 is in use, however, and the inner surface of optical sensor 210 or further raised portion 260 may be in contact with (or pressed against) the targeted area of the user's body, the contact or pressure between the targeted area of the user and one or more discrete components of optical sensor 210 may serve to compress one or more resilient members 630. This compression may, in turn, result in an increasing level of contact or pressure between the one or more discrete components of optical sensor 210 and the targeted area of the user's body.

Among the advantages to the embodiment depicted in FIG. 8, the adjustment of the protrusion height of each discrete component of optical sensor 210 relative to the remainder of caseback 220 or raised portion 250 may be automated, i.e., requires little or no intervention by the user apart from the user's securing of apparatus 100 to the targeted area of the user via, for example, bands 130. For example, as the user secures apparatus 100 to the targeted area of the user, one or more discrete components of optical sensor 210 may come into contact with the user's body and compress corresponding resilient members 630. The resilient members' spring urging of the associated discrete component of optical sensor 210 against the user may result in the respective discrete component maintaining a desirable level of contact or pressure between the inner surface of optical sensor 210 and the targeted area.

Moreover, because each discrete component of optical sensor 210 enjoys at least one degree of freedom with respect to the other discrete components and may be permitted to move toward or away from the targeted area of the user independent of the other discrete components, optical sensor 210 may contour to the targeted area. Thus, each discrete component of optical sensor 210 (i.e., lateral components 810, 830 and intermediate component 820) may be maintained in close contact with the targeted area and, as a result, may provide more accurate or reliable information to apparatus 100 regarding the physiological parameter being measured.

Figure 9:
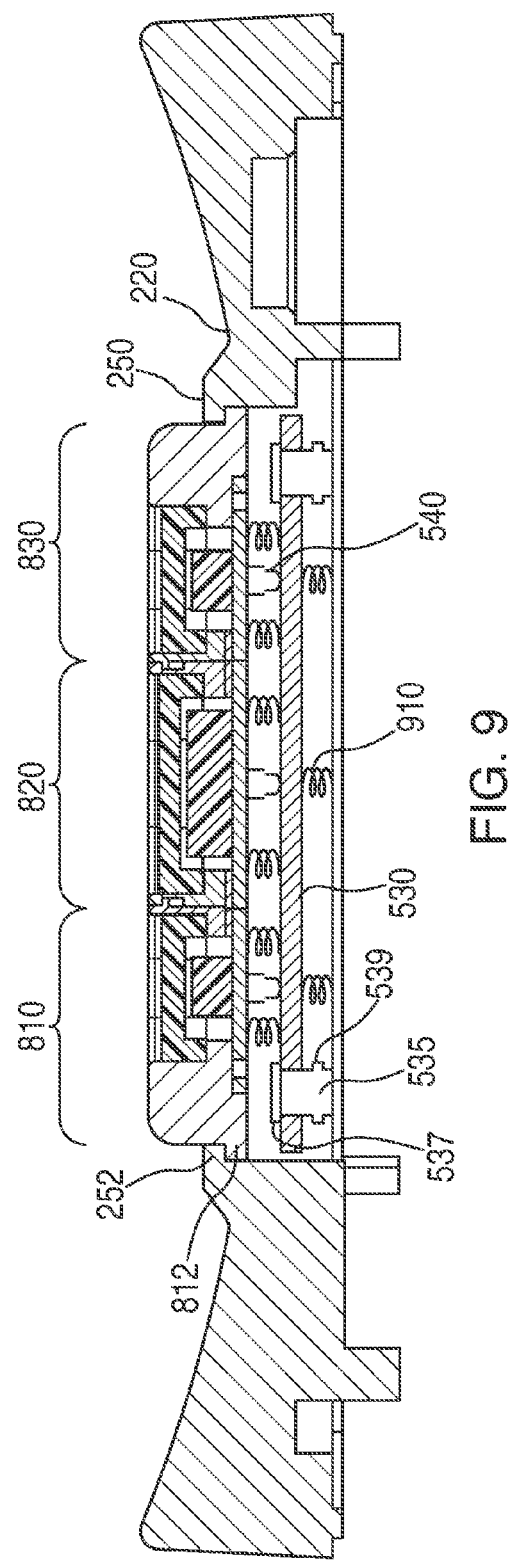
FIG. 9 depicts some aspects of an illustrative embodiment of an apparatus as described herein.

FIG. 9 depicts a cross-sectional view of another embodiment of apparatus 100. In one aspect, the embodiment depicted in FIG. 9 may be substantially similar to the embodiment depicted in FIG. 8. In one aspect, however, circuit board 530 may be afforded at least one degree of freedom and the ability to move toward and away from the targeted area of the user's body in response to a level of contact or pressure between optical sensor 210 and the targeted area.

In one aspect, circuit board 530 may be coupled to, or otherwise in contact with, one or more resilient members 910. One or more resilient members 910 may be substantially similar to one or more resilient members 630 located between circuit board 530 and sub-boards 512, 514, and 516. Resilient members 910 may serve, among other things, to spring urge circuit board 530 toward the targeted area of the user and allow circuit board 530 to move toward the outer surface of caseback 220 in response to contact or pressure applied by the targeted area at the inner surface of optical sensor 210.

In another aspect, circuit board 530 may slide or translate along placement posts 535. Placement posts 535 may comprise a longitudinal shaft having a lip 537 at or proximate to an end of posts 535 nearest sub-boards 512, 514, and 516. Lip 537 may serve to retain circuit board 530 on placement posts 535 against the force of resilient members 910. In other embodiments, placement posts 535 may comprise a pin or some other type of fixed or removable protrusion that may prevent circuit board 530 from advancing toward sub-boards 512, 514, and 516 beyond the length of posts 535. In further embodiments, placement posts 535 may comprise any structure, feature, or component to adequately retain circuit board 530 on posts 535 against the force of resilient members 910.

Placement posts 535 may further comprise a similar lip 539 located along the longitudinal extension of placement posts 535 near or proximate to the outermost surface of caseback 220 (i.e., the surface farthest from the targeted area of the user). Lip 539 may serve to provide a maximum displacement of circuit board 530 in response to a level of contact or pressure between the inner surface of optical sensor 210 and the targeted area of the user. In other embodiments, placement posts 535 may comprise a pin or some other type of fixed or removable protrusion that may prevent circuit board 530 from moving toward the outermost surface of caseback 220 beyond a desirable location. In further embodiments, placement posts 535 may comprise any structure, feature, or component to adequately prevent circuit board 530 from moving closer than a desirable minimum distance from the outermost surface of caseback 220. In still further embodiments, placement posts 535 may have no lip, protrusion, structure, feature, or component for preventing circuit board 530 from moving closer than a desirable minimum distance with the outermost surface of caseback 220. Rather, the maximum deflection or compression of resilient members 910 may serve to restrain circuit board 530 from moving closer than a desirable minimum distance from the outermost surface of caseback 220.

Similar to one or more resilient members 630, one or more resilient members 910 may be a spring. In further embodiments, one or more resilient members 910 may be a compression spring, constant spring, variable spring, cantilever spring, helical spring, leaf spring, or some other suitable spring. In such embodiments, the one or more springs may exhibit a predetermined spring constant (k) suitable for use in apparatus 100 and/or affording a proper amount of resistance or contact pressure between optical sensor 210 and the targeted area of the user's body.

In some embodiments, the spring constant (k) for one or more resilient members 910 may vary from the spring constant for one or more resilient members 630. For example, resilient members 910 may have a higher spring constant (i.e., stiffer springs offering greater resistance to depression) than resilient members 630 (i.e., weaker springs offering less resistance to depression). In such embodiments, a first level of contact or pressure between the inner surface of optical sensor 210 and the targeted area of the user may result in displacement only of resilient members 630. At a second level of contact, however, (e.g., when resilient members 630 have reached a maximum deflection/depression), additional resistance and deflection may be afforded by resilient members 910. Of course, other embodiments are also possible, including embodiments in which one or more resilient members 630 may be associated with a stiffer spring compared to one or more resilient members 910.

When the embodiment of apparatus 100 depicted in FIG. 9 is not being worn by a user and/or no pressure is applied to the inner surface of optical sensor 210 or further raised portion 260 by the targeted area of the user, optical sensor 210 may be spring urged away from the outermost surface of caseback 220 by a combination of resilient members 630 and resilient members 910. Optical sensor 210 and/or further raised portion 260 may be retained in apparatus 100 in an inwardly-urged position in a similar manner to that described above with respect to FIG. 8 (in embodiments where optical sensor 210 comprises three discrete components) or in a similar manner to that described above with respect to FIG. 7 (in embodiments in which optical sensor 210 does not comprise a plurality of independent components).

When the embodiment of apparatus 100 depicted in FIG. 9 is in use, however, and the inner surface of optical sensor 210 or further raised portion 260 may be in contact with (or pressed against) the targeted area of the user's body, the contact or pressure between the targeted area of the user and the inner surface of optical sensor 210 may serve to compress one or more resilient members 630 and one or more resilient members 910. In an embodiments where the spring constant associated with one or more resilient members 910 may be greater than the spring constant associated with one or more resilient members 630, the user may experience a first level of resistance with respect to compression of optical sensor 210 and pressure at the targeted area up to a first level of contact or pressure between the inner surface of optical sensor 210 and the targeted area, and then a second level of resistance with respect to compression of optical sensor 210 and pressure at the targeted area. This increasing resistance may, in turn, result in an increasing level of contact or pressure between the components of optical sensor 210 (e.g., LEDs 232/lenses 234 and photodiode 242/lens 244) and the targeted area of the user's body.

Similar to the embodiments depicted in FIGS. 7 and 8, the adjustment of the protrusion height of optical sensor 210 relative to the remainder of caseback 220 or raised portion 250 in the embodiment depicted in FIG. 9 may be automated, i.e., requires little or no intervention by the user apart from the user's securing of apparatus 100 to the targeted area of the user via, for example, bands 130. For example, as the user secures apparatus 100 to the targeted area of the user, optical sensor 210 may come into contact with the user's body and compress corresponding resilient members 630 and 910. The resilient members' spring urging of optical sensor 210 against the targeted area of the user may result in a desirable level of contact or pressure between the inner surface of optical sensor 210 and the targeted area.

It should be noted that the multi-level spring configuration (i.e., embodiments comprising resilient members 630 and 910) depicted in FIG. 9 may be implemented in conjunction with any other embodiment described herein, including the embodiments depicted in FIGS. 6-8. Moreover, circuit board 530 may comprise one or more sub-boards similar to circuit board 510 depicted in FIGS. 8 and 9.

FIG. 10 depicts a cross-sectional view of another embodiment of apparatus 100. In one aspect, the embodiment depicted in FIG. 10 may be substantially similar to the embodiment depicted in FIG. 7. In the embodiment of FIG. 10, however, apparatus 100 may comprise a band, a strap, a bracelet, or some other wearable device that may be worn at the user's wrist, arm, or other extremity. For example, apparatus 100 may be, but is not limited to, a fitness band, a health monitoring device, or an activity tracker. Moreover, optical sensor 210 may not be positioned within a watch caseback or rigid housing of a wearable device. Rather, optical sensor 210 may be incorporated into a strap 1010 of any wearable device.

In one embodiment, strap 1010 may comprise a pliable or flexible material suitable for substantially conforming to a user's body. For example, strap 1010 may comprise a flexible polymer, silicone, or plastic material. Alternatively, strap 1010 may comprise a fabric or woven material. In other embodiments, strap 1010 may be a rigid or semi-rigid material, such as a plastic or metallic material, molded so as to substantially conform to the user's body. Strap 1010 may also comprise one or more layers such as an outer layer 1012 (i.e., a layer farthest from the targeted area) and an inner layer 1014 (i.e., a layer closest to the targeted area). In some embodiments, layers 1012 and 1014 may be joined or bonded together using any suitable means, including but not limited to, a glue, an epoxy, a bonding agent, or other suitable substances or objects. In other embodiments, strap 1010 may comprise a single layer rather than two or more adjacent layers.

Regardless of the material(s) comprising strap 1010 and/or the number of layers comprising strap 1010, strap 1010 may be formed so as to define a cavity, aperture, or recess within which optical sensor 210 and/or a raised portion 1020 may be positioned. One or more circuit boards may also be positioned within the cavity, aperture, or recess. As noted above with respect to other embodiments, apparatus 100 may comprise two or more circuit boards (e.g., circuit boards 510 and 530 depicted in FIGS. 5A and 6-9). FIG. 10 depicts an embodiment with only circuit board 510, but should not be construed to exclude embodiments with additional circuit boards located within the cavity, aperture, or recess (e.g., above, below, adjacent, or aside circuit board 510). It should also be noted that the embodiment depicted in FIG. 10 may comprise additional circuit boards located elsewhere along strap 1010. For example, the embodiment depicted in FIG. 10 may comprise a second circuit board 530 positioned within a second cavity, aperture, or recess along strap 1010. Alternatively, some embodiments may comprise a second circuit board 530 positioned at or near a buckle or latch at which two opposing portions or ends of strap 1010 may be joined when apparatus 100 is in use. In embodiments comprising two or more circuit boards, the boards may be in communication with one another through any suitable wired or wireless communication channel.

In one aspect, optical sensor 210 may be positioned within raised portion 1020. Raised portion 1020 may be in contact and/or positioned within the cavity, aperture, or recess of strap 1010 such that raised portion 250 may slide or translate in a direction toward or away from the targeted area of the user with respect to the cavity, aperture, or recess.

In one embodiment, raised portion 1020 may comprise a lip 1022 at the outer surface of raised portion 1020, i.e., the surface closest to circuit board 510 and farthest from the targeted area of the user. In one embodiment, lip 1022 may extend radially outward from raised portion 1020 so as to create an abutment surface 1022a at the innermost (closest to the targeted area) surface of lip 1022.

In another aspect, strap 1010 may comprise an opposing lip 1016 at the inner surface of strap 1010, i.e., the surface positioned closest to the targeted area of the user. Opposing lip 1016 may extend radially inward from strap 1010 toward the cavity, aperture, or recess so as to create an opposing abutment surface 1016a at the outermost (farthest from the targeted area) surface of lip 1016.

In a further aspect, and similar to the embodiment depicted in FIG. 7, one or more resilient members 630 may be positioned between an outer portion of strap 1010 and circuit board 510. FIG. 10 depicts two resilient members. Other embodiments, however, may comprise fewer or additional resilient members.

Resilient members 630 may, among other things, serve to urge circuit board 510, optical sensor 210, and/or raised portion 1020 toward the targeted area of the user's body. In one embodiment, one or more resilient members 630 may be a spring. In further embodiments, one or more resilient members may be a compression spring, constant spring, variable spring, cantilever spring, helical spring, leaf spring, or some other suitable spring. In such embodiments, the one or more springs may exhibit a predetermined spring constant (k) suitable for use in apparatus 100 and/or affording a proper amount of resistance or contact pressure between raised portion 1020/optical sensor 210 and the targeted area of the user's body.

The one or more resilient members may urge raised portion 1020 (and/or circuit board 510 and optical sensor 210) inward toward the targeted area. Raised portion 1020 (and/or circuit board 510 and optical sensor 210) may be retained in apparatus 100, however, by an engagement or abutment of lip 1022 of raised portion 1020 with opposing lip 1012 of strap 1010.

In this manner, when apparatus 100 is not being worn by a user and no pressure is applied to the inner surface of raised portion 1020 by the targeted area of the user, raised portion 1020 may be spring urged away from the outer portion of strap 1010 and retained in an inwardly-urged position by the engagement or contact between lip 1022 of raised portion 1020 and opposing lip 1016 of strap 1010. When apparatus 100 is in use, however, and the inner surface of raised portion 1020 may be in contact with (or pressed against) the targeted area of the user's body, the contact or pressure between the targeted area of the user and raised portion 1020 may compress one or more resilient members 630. This compression may, in turn, result in an increasing level of contact or pressure between optical sensor 210 (at the inner surface of raised portion 1020) and the targeted area of the user's body.

Among the advantages to the embodiment depicted in FIG. 10, the adjustment of the protrusion height of raised portion 1020 relative to the inner surface of strap 1010 may be automated, i.e., may require little or no intervention by the user apart from the user's securing of apparatus 100 to the targeted area of the user via, for example, a joinder of opposing portions of strap 1010. For example, as the user secures apparatus 100 to the targeted area of the user, raised portion 1020 and/or optical sensor 210 may come into contact with the user's body and compress resilient members 630. Nonetheless, the resilient members spring urging of raised portion 1020 toward the user may result in optical sensor 210 maintaining an adequate level of contact or pressure against the targeted area.

It should be noted, however, that although the mechanisms depicted in FIG. 10 for adjustment of the protrusion height of optical sensor 210 may be substantially similar to those depicted in FIG. 7, any of the features of any of the aforementioned embodiments (e.g., any of the embodiments described with respect to FIGS. 5-9) may be incorporated into an embodiment substantially similar to the embodiment depicted in FIG. 10. Thus, some embodiments of the apparatus depicted in FIG. 10 may comprise a threaded interface between raised portion 1020 and strap 1010 such that the protrusion height of raised portion 1020 relative to strap 1010 may be controlled through a rotation of raised portion 1020. Other embodiments may comprise an adjustment ring positioned, for example, between raised portion 1020 and strap 1010, substantially similar to the adjustment ring depicted in FIG. 6. In still further embodiments of the apparatus depicted in FIG. 10, optical sensor 210 may comprise two or more portions, the protrusion height of each may be adjusted independently of the others, substantially similar to the independent optical sensor portions depicted in FIG. 8. One or more layers of resilient members, such as those depicted in FIG. 9, may also be implemented in the embodiment depicted in FIG. 10.

While illustrative embodiments have been illustrated and described, it will be appreciated that various changes can be made therein without departing from the spirit and scope of the disclosure. Moreover, the various features of the embodiments described herein are not mutually exclusive. Rather any feature of any embodiment described herein may be incorporated into any other suitable embodiment.

Additional features may also be incorporated into the described systems and methods to improve their functionality. For example, those skilled in the art will recognize that the disclosure can be practiced with a variety of physiological monitoring devices, including but not limited to heart rate and blood pressure monitors, and that various light emitting and photo detecting devices may be employed. The devices may or may not comprise one or more features to ensure they are water resistant or waterproof. Some embodiments may of the devices may hermetically sealed.

In some embodiments, it may be appropriate to use one or more lenses that are configured for receiving more than one optical sensor in a single lens and/or to use one or more lenses that are configured for receiving more than one light source in a single lens. Furthermore, while FIGS. 1-9 depict a number of watch-like embodiments, other embodiments may comprise fewer, additional, or alternative features similar to fitness bands and/or other wearable devices for physiological monitoring (e.g., the embodiment depicted in FIG. 10).

Other embodiments of the aforementioned systems and methods will be apparent to those skilled in the art from consideration of the specification and practice of this disclosure. It is intended that the specification and the aforementioned examples and embodiments be considered as illustrative only, with the true scope and spirit of the disclosure being indicated by the following claims.

What is claimed is:

1. An apparatus for detecting a physiological parameter of a user, the apparatus comprising:
    a housing comprising an optical sensor, a contact surface of the housing configured for placement proximate a targeted area of a user's body;
    a strap for securing the housing to the targeted area,
    the optical sensor comprising at least one light source and an optical detector, at least a portion of the optical sensor configured for placement proximate the contact surface;
    at least one substrate, the light source and the optical detector coupled to an upper surface of the at least one substrate;
    an opaque member coupled to the upper surface of the substrate and positioned between the light source and the optical detector; and
    at least one optical barrier positioned between the light source and the optical detector, the at least one optical barrier comprising a laterally extending leg and a vertically extending leg, the laterally extending leg being coupled to the opaque layer and positioned between the light source and the optical detector, the vertically extending leg being substantially perpendicular with respect to the laterally extending leg and extending from the laterally extending leg to a contact portion, the contact surface of the housing comprising the contact portion of the at least one optical barrier.

2. The apparatus of claim 1, wherein the optical sensor comprises:
    a pair of light sources, each positioned on opposing sides of the optical detector;
    a pair of opaque members, each coupled to the at least one substrate and each positioned on opposing sides of the optical detector; and
    a pair of optical barriers, each coupled to a respective opaque layer and positioned between the optical detector and a respective one of the pair of light sources.

3. The apparatus of claim 1, wherein the optical sensor further comprises at least one lens, the at least one lens comprising an outer surface substantially coplanar with the contact surface of the housing.

4. The apparatus of claim 3, wherein the at least one lens comprises a plurality of lenses, each lens associated with a respective light source or optical detector.

5. The apparatus of claim 3, wherein the at least one lens comprises a glass or plastic lens.

6. The apparatus of claim 5, wherein the at least one lens comprises an epoxy lens at least partially encapsulating at least one of the light source or optical detector.

7. The apparatus of claim 6, wherein the at least one optical barrier is configured to receive the epoxy lens in a liquid or gel state.

8. A method for providing a physiological parameter sensor, the method comprising:
    providing a wearable device comprising a housing, the housing comprising a contact surface configured for placement adjacent a targeted area of a user's body;
    inserting at least a portion of an optical sensor within the housing, the optical sensor comprising at least one light source and at least one optical detector;
    providing a substrate, the at least one light source and the at least one optical detector each coupled to an upper surface of the substrate;
    providing a pliant member coupled to the upper surface of the substrate and positioned between the at least one light source and the at least one optical detector;

providing at least one optical barrier between the at least one light source and the at least one optical detector, the at least one optical barrier comprising a laterally extending segment and a vertically extending segment, the laterally extending segment being coupled to the pliant member and positioned between the at least one light source and the at least one optical detector, the vertically extending segment being substantially perpendicular with respect to the laterally extending segment and extending from the laterally extending segment to a contact portion, the contact surface comprising an aperture, the contact portion of the at least one optical barrier at least partially defining the aperture; and inserting at least a portion of a lens within the aperture.

9. The method of claim 8, wherein the at least one optical barrier is integral with the housing and the at least one optical barrier extends from the contact portion downward toward a base portion of the at least one light source or the at least one optical detector.

10. The method of claim 8, wherein inserting at least a portion of a lens within the aperture comprises inserting at least a portion of a glass or plastic lens within the aperture.

11. The method of claim 8, wherein inserting at least a portion of a lens within the aperture comprises:
pouring a liquid or gel epoxy within the aperture; and
allowing the epoxy to solidify within the aperture such that the solid epoxy at least partially encapsulates the at least one light source or the at least one optical detector.

12. The method of claim 8, further comprising:
coupling the at least one light source and the at least one optical detector to the substrate prior to inserting at least the portion of the optical sensor within the housing.

13. An optical sensor for measuring a physiological parameter, the sensor comprising:
a housing comprising a contact surface configured for placement proximate a tissue area;
at least one light source;
at least one optical detector;
at least one substrate, the at least one light source and the at least one optical detector being coupled to an upper surface of the at least one substrate;
at least one opaque member coupled to the upper surface of the at least one substrate and positioned between the at least one light source and the at least one optical detector; and
at least one optical barrier integral with the housing and at least partially defining an aperture in the contact surface, the at least one optical barrier comprising a laterally extending portion and a vertically extending portion, the laterally extending portion being coupled to the opaque member and positioned between the at least one light source and the at least one optical detector, the vertically extending portion being substantially perpendicular with respect to the laterally extending portion and extending from the laterally extending portion to a contact portion, the contact surface of the housing comprising the contact portion of the at least one optical barrier.

14. The sensor of claim 13, wherein the vertically extending portion of the optical barrier comprises at least one abutment surface.

15. The sensor of claim 14, wherein the at least one abutment surface is configured for receiving or retaining a lens, the lens configured to receive at least a portion of the at least one light source or the at least one light detector.

* * * * *